United States Patent [19]
Böck et al.

[11] Patent Number: 5,830,720
[45] Date of Patent: Nov. 3, 1998

[54] RECOMBINANT DNA AND EXPRESSION VECTOR FOR THE REPRESSIBLE AND INDUCIBLE EXPRESSION OF FOREIGN GENES

[75] Inventors: August Böck, Geltendorf; Robert Gary Sawers, München; Michael Jarsch, Bad Heilbrunn; Roland Herbst, Munich, all of Germany

[73] Assignee: Boehringer Mannheim GmbH, Mannheim, Germany

[21] Appl. No.: 386,198

[22] Filed: Feb. 9, 1995

Related U.S. Application Data

[63] Continuation of Ser. No. 8,311, Jan. 25, 1993, abandoned, which is a continuation-in-part of Ser. No. 503,593, Apr. 3, 1990, abandoned.

[30] Foreign Application Priority Data

Apr. 21, 1989 [DE] Germany .......................... 39 13 201.3
Aug. 7, 1989 [DE] Germany .......................... 39 26 076.3

[51] Int. Cl.$^6$ .............................. C12N 15/63; C12N 1/21; C07H 21/04; C12P 21/02
[52] U.S. Cl. .................. 435/172.1; 235/69.1; 235/252.3; 235/253.33; 235/252.34; 536/23.1; 536/24.1
[58] Field of Search .............................. 435/172.1, 172.3, 435/69.1, 183, 257.3, 257.33, 252.34, 254.11, 320.1; 536/23.1, 23.2, 23.5, 23.7, 24.1

[56] References Cited

U.S. PATENT DOCUMENTS

| | | | |
|---|---|---|---|
| 4,628,027 | 12/1986 | Gay | ......................................... 435/7.23 |
| 4,767,843 | 8/1988 | Yazaki et al. | ...................... 530/388.26 |
| 5,071,963 | 12/1991 | Revel et al. | .......................... 530/387.9 |

FOREIGN PATENT DOCUMENTS 0 285 152  10/1988  European Pat. Off. .

OTHER PUBLICATIONS

Maniatis et al. "Molecular Cloning: A Laboratory Manual" (Cold Spring Harbor Laboratory Press, Cold Spring Harbor, N.Y.) pp. 403–433 1982.

Jayaraman et al., *Molecular Microbiology*, "The nirB promotor of *Escherichia coli*: location of nucleotide sequences essential for regulation by oxygen, the FNR protein and nitrite", (1988) 2(4), pp. 527–530.

Li et al., *Journal of Bacteriology*, "Promotor Region of the nar Operon of *Escherichia coli* Nucleotide Sequence and Transcription Initiation Signals", Oct. vol. 169, No. 10, Oct. 1987, pp. 4614–1620.

Sawers et al., "Anaerobic Regulation of Pyruvate Formate–Lyase from *Escherichia coli* K–12", *Journal of Bacteriology*, Band 170, Nov. 11, 1988, pp. 5330–5336.

Sawers et al., "Novel Transcriptional Control of the Pyruvate Formate–Lyase Gene: Upstream Regulatory Sequences and Multiple Promoters Regulate Anaerobic Expression", *Journal of Bacteriology*, Band 171, May 5, 1989, pp. 2485–2498.

Biological Abstract v. 75(11), 1983, Abstract No. 80078.

Biochemistry, 1983, vol. 22, pp. 5858–5868, Robert McCarrol et al, "Nucleotide Sequence of the Dictyostelium discoideum Small–Subunit Ribosomal Ribonucletic Acid Inferred from the Gene Sequence: Evolutionary Implications".

Journal of Bacteriology, May 1989, vol. 171, No. 5 pp. 2485–2498, by Sawyers and Bock, "Novel Transcriptional Control of the Pyruvate Formate–Lyase Gene: Upstream Regulatory Sequence and Multiple Promoters Regulate Anaerobic Expression".

Archives of Microbiology, 1982, vol. 132, pp. 365–371, by Pecher et al., "Expression of Pyruvate Formate–Lyase of *Escherichia coli* from the Cloned Structural Gene".

*Primary Examiner*—Nancy Degen
*Attorney, Agent, or Firm*—Nikaido, Marmelstein, Murray & Oram LLP

[57] ABSTRACT

The recombinant DNA according to the present invention contains a regulator region which is different from the pfl gene; a promoter region upstream from the gene which contains a −35/−10 promoter sequence; a regulator region upstream from the promoter region which contains a sequence (I) 5'-GAGATATGATCTATATCAATTTC-3' or a 23 base pair sequence which is at least 80% identical to positions 6–10 and 15–19 of said sequence (I) but not having C at position 8 and/or G at position 17. An expression vector according to the present invention contains a recombinant DNA according to the present invention ligated into a suitable vector molecule and methods are also described for expression the DNA.

31 Claims, 12 Drawing Sheets

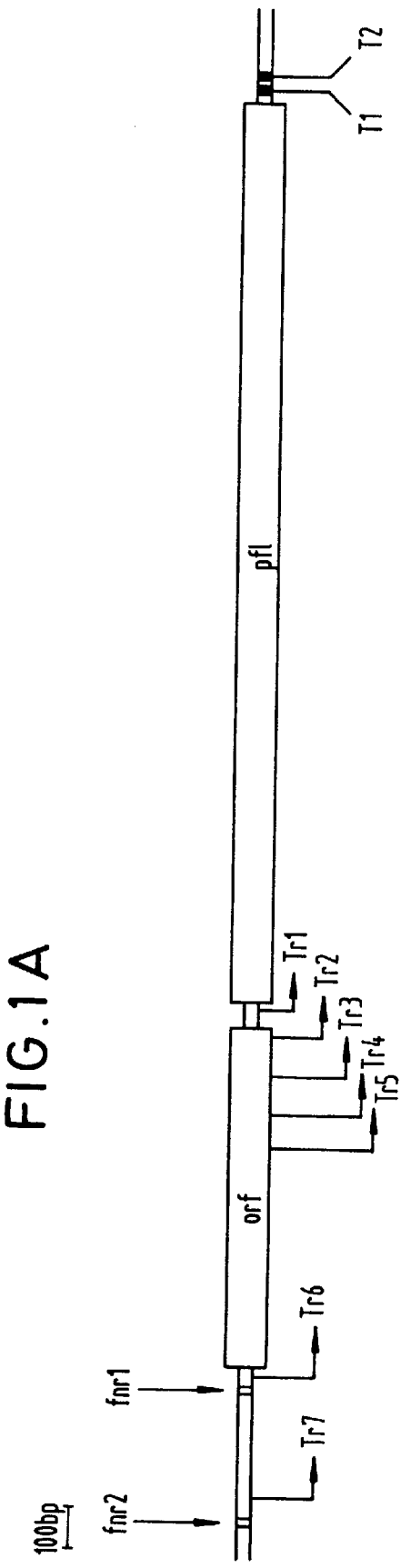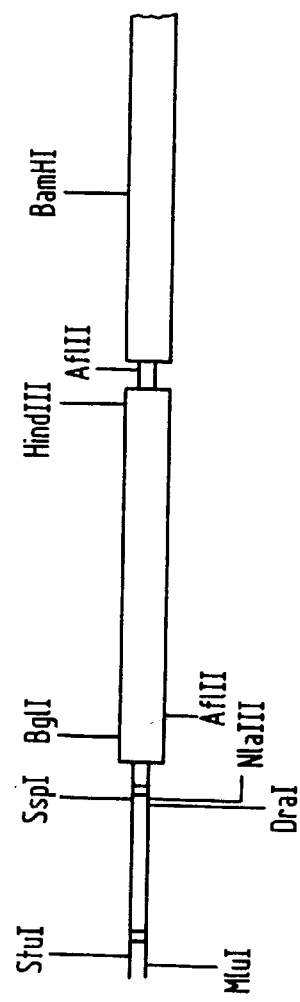
FIG.1A
FIG.1B

FIG. 10

Sequence of the pfl promoter

```
ACGCGTTTGCTGCACATCAGTCGTTGTTGAAGGCCTACGAAAAGCTGCAGCGCGCCAAAG
CAGCATTCTGGGCAAAATAAAATCAAATAGCCTACGCAATGTAGGCTTAATGATTAGTCT
GAGTTATATTACGGGGCGTTTTTTTAATGCCCCGCTTTACATATATTTGCATTAATAAAA
TAATTGTAATTATAAGGTTAAATATCGGTAATTTGTATTTAATAAATACGATCGATATTG
TTACTTTATTCGCCTGATGCTCCCTTTTAATTAACTGTTTTAGCGGAGGATGCGGAAAAA
ATTCAACTCATTTGTTAATTTTTAAAATTTATTTTTATTTGGATAATCAAATATTTACTC
CGTATTTGCATAAAAACCATGCGAGTTACGGGCCTATAAGCCAGGCGAGATATGATCTAT
ATCAATTTCTCATCTATAATGCTTTGTTAGTATCTCGTCGCCGACTTAATAAAGAGAGAG
TTAGTGTGAAAGCTGACAACCCTTTTGATCTTTTACTTCCTGCTGCAATGGCCAAAGTGG
CCGAAGAGGCGGGTGTCTATAAAGCAACGAAACATCCGCTTAAGACTTTCTATCTGGCGA
TTACCGCCGGTGTTTTCATCTCAATCGCATTCGTCTTCTATATCACAGCAACCACTGGCA
CAGGCACAATGCCCTTCGGCATGGCAAAACTGGTTGGCGGCATTTGCTTCTCTCTGGGGC
TGATTCTTTGTGTTGTCTGCGGAGCCGATCTCTTTACTTCCACCGTGTTGATTGTTGTTG
CTAAGGCGAGTGGGCGCATCACCTGGGGTCAGTTGGCGAAAAACTGGCTAAATGTCTATT
TTGGCAACCTGGTCGGCGCACTGCTGTTTGTACTTTTAATGTGGCTTTCCGGCGAGTATA
TGACCGCAAATGGTCAATGGGACTAAACGTCCTACAAACCGCCGACCACAAAGTGCACC
ATACTTTTATTGAGGCCGTCTGTCTTGGTATCCTGGCAAACCTGATGGTATGTCTGGCAG
TATGGATGAGTTATTCTGGCCGCAGCCTGATGGACAAAGCGTTCATTATGGTGCTGCCGG
TCGCGATGTTTGTTGCCAGCGGTTTTGAGCACAGTATCGCAAACATGTTTATGATCCCGA
TGGGTATTGTAATCCGCGACTTCGCATCCCCGGAATTTTGGACCGCAGTCGGTTCTGCAC
CGGAAAATTTTTCTCACCTGACCGTGATGAATTTCATCACTGATAACCTGATTCCGGTTA
CGATCGGCAACATTATCGGTGGTGGTTTGTTGGTTGGGTTGACATACTGGGTCATTTACC
TGCGTGAAAACGACCACCATTAATGGTTGTCGAAGTACGCAGTAAATAAAAAATCCACTT
AAGAAGGTAGGTGTTACATGTCCGAGCTTAATGAAAGTTAGCCACAGCCTGGGAAGGTT
TTACCAAAGGTGACTGGCAGAATGAAGTAAACGTCCGTGACTTCATTCAGAAAAACTACA
CTCCGTACGAGGGTGACGAGTCCTTCCTGGCTGGCGCTACTGAAGCGACCACCACCCTGT
GGGACAAAGTAATGGAAGGCGTTAAACTGGAAAACCGCACTCACGCGCCAGTTGACTTTG
ACACCGCTGTTGCTTCCACCATCACCTCTCACGACGCTGGCTACATCAACAAGCAGCTTG
AGAAAATCGTTGGTCTGCAGACTGAAGCTCCGCTGAAACGTGCTCTTATCCCGTTCGGTG
GTATCAAAATGATCGAAGGTTCCTGCAAAGCGTACAACCGCGAACTGGATCC
```

FIG. 11

| | Promoter region for |
|---|---|
| -40　　　　-30　　　　-20　　　　-10　　　　+1<br>AATGT<u>AGGCTT</u>AATGATTAGTCTGAGT<u>TATATT</u>ACGGGCG | Transcript 7. |
| TATCAAT<u>TTCTCA</u>TCTATAATGCTTTG<u>TTAGTA</u>TCTCGTCG | Transcript 6. |
| TGGTATCC<u>TGGCAA</u>ACCTGATGGTA<u>TGTCTG</u>GCAGTATGGA | Transcript 5. |
| GTTCATTA<u>TGGTGC</u>TGCCGGTCGCGAT<u>GTTTGT</u>TGCCAGCG | Transcript 4. |
| CGGAATTT<u>TGGACC</u>GCAGTCGGTTCTGCACCGGAAAATTTT | Transcript 3. |
| CATTATCGGT<u>GGTGGT</u>TTGTTGGTTGGG<u>TTGACA</u>TACTGGG | Transcript 2. |
| ACCACCATTAA<u>TGGTTG</u>TCGAAGTACGCAG<u>TAAAT</u>AAAAAA | Transcript 1. |

RECOMBINANT DNA AND EXPRESSION VECTOR FOR THE REPRESSIBLE AND INDUCIBLE EXPRESSION OF FOREIGN GENES

This application is a continuation of application Ser. No. 08/008,311 filed Jan. 25, 1993, now abandoned which is a continuation-in-part of application Ser. No. 03/503/593, filed Apr. 3, 1990, now abandoned.

DESCRIPTION

Recombinant DNA for the repressible and inducible expression of foreign genes.

The invention concerns recombinant DNA and expression vectors, processes for the production of such recombinant DNA and expression vectors, as well as their use for the inducible and repressible expression of a foreign gene.

An important aim of applied genetic engineering is the production of proteins from recombinant DNA. A special class of vectors, the so-called expression vectors, are necessary for this. These have not only the structural requirements for the cloning, the transfer and the multiplication of the recombinant DNA, but also for the expression of the protein. These recombinant DNA molecules contain special regulation sequences for this, the promoters, which effect the transcription of the DNA sequence into RNA, the translation of which by the ribosomes leads to the finished protein.

DNA regions, to which bacterial RNA polymerase binds, for the transcription of one or more genes are designated promoters. Many of these promoters have structures in common which are presumed to be important, inter alia, for interactions with particular proteins. Such interactions with cellular proteins or other molecules can cause a repression, or also an induction, of the activity of a promoter. An example of this is the interaction of the lambda promoter $P_l$ with the lambda repressor cI.

In the production of proteins by genetic engineering, it is particularly advantageous if a promoter present in an expression vector can be regulated by the presence or addition of a repressor or inducer.

This regulation can be effected by suppressing the activity of the promoter at the beginning of the fermentation so that a large biomass can be produced with only minimal impairment of the vitality of the cells. Subsequently, the promoter is stimulated by suitable means and the synthesis of the product can then take place. Thus the fermentation process may be basically divided into a growth phase and a production phase.

The $P_L$ promoter of the bacteriophage lambda, the lac promoter, the trp promoter, the tac promoter, the trc promoter and the rac promoter may, for example, be used for the controllable gene expression.

These expression systems are, however, only of limited suitability for a large-scale technical application. Above all, a temperature increase to 42° C., which is necessary for the induction of the lambda $P_L$ promoter, is very difficult in a technical application with volumes of more than 50 l. In addition, it has been shown that the induction of the lambda $P_L$ promoter has to take place at an early stage of the growth phase and it is therefore possible that not enough biomass is obtained for a large-scale production.

When using the lac promoter for expression vectors it is not possible, in contrast to the $P_L$ promoter, to completely repress the system using a copy of the repressor gene because the repressor is titrated by the copy number of the lac operator. Although the repression can be re-established by the use of repressor over-producers, such strains are only partially inducible. If the expression vector does not contain the corresponding repressor gene then one is limited in the selection of host strains for lambda $P_L$, for lac and the other derivatives of the lac promoter. Moreover, the addition of inducers during the fermentation, which is necessary in these systems, is not only expensive but also causes fundamental difficulties, above all if inducers which can be metabolized, e.g. lactose, are concerned.

The trp promoter is also a system which cannot be completely repressed. The addition of tryptophan for the repression also considerably increases the cost of the fermentation as is the case when using inducers.

The inducers known up to now are therefore only of limited suitability for an industrial application since these inducers are in general very expensive and the methods used for induction or repression are complicated and are only of limited suitability for the regulation of the repression of a protein.

A promoter which can be repressed by oxygen is known from DE-A 37 10 633 which originates from the fdhF gene and can be induced by formate. With this a simple repression and induction is indeed possible; however, it is a relatively weak promoter.

It is therefore the object of this invention to provide recombinant DNA and expression vectors which enable a regulation of the expression and synthesis of a desired gene product in a simple manner as well as a particularly high expression rate of the gene.

This object is achieved by a recombinant DNA which is characterized in that it contains:

a) a regulator region which is at least 50% homologous to the sections −969 to −991 base pairs and/or −1308 to −1330 base pairs of the sequence of FIG. 10 and b) a promoter region in the 3' direction from the regulation sequence which has a −35/−10 promoter-consensus sequence (Rosenberg, M. and Court, D. (1979) Ann. Rev. Genet. 13: 319–353).

In a preferred embodiment of the invention the regulator region is at least 65% homologous to the above-mentioned sequences in FIG. 10.

The numbering of the bases in this connection relates to the ATG start codon of the pfl gene as +1 (for adenine) which is underlined in FIG. 10. Nucleotides which are on the 5' side of this have negative numbers.

In a further preferred embodiment of the invention the recombinant DNA contains in addition at least a third sequence which is at least 80% homologous to the following consensus sequence:(SEQ ID NO:1)

```
       C  T
TATTTG AT AA
       G  -
```

The term "homologous" or "identical" as used herein means percentage match utilizing the best match and accounting for gaps.

This third sequence can thereby be included once or several fold in the recombinant DNA.

Suitable promoters of the promoter region of the recombinant DNA according to the present invention are all promoters which contain a consensus sequence as defined above in the −35/−10 region. These are, e.g. the lac promoter, lambda $P_L$ promoter, trp promoter, mgl promoter (EPA 285152) or the promoters from FIG. 11 or 50%, and preferably 65% homologues thereof.

A sequence is preferably used as the promoter region which is 50% and particularly preferably 65% homologous to one of the sequences shown in FIG. 11.

In an especially preferred embodiment at least one of the promoters from transcript 6 and transcript 7 is used which have the sequences shown in FIG. 11.

The object of the invention is also achieved by a recombinant DNA, comprising a gene to be expressed which is different from the pfl gene; a promoter region upstream from said gene which contains a −35/−10 promoter sequence; a regulator region upstream from said promoter region which contains a sequence (I)(SEQ ID NO:2)

5'-GAGATATGATCTATATCAATTTC-3'      (I)

or a 23 base pair sequence which is at least 80% identical to position 6–10 and 15–19 of said sequence (I) but not having C at position 8 and/or G at position 17.

The aforementioned recombinant DNA may also further comprise a sequence which is at least 80% identical to the following consensus sequence:(SEQ ID NO:1)

```
        C  T
TATTTG  AT AA.
        G  -
```

The regulator region preferably also contains a sequence which is at least 50% identical to a sequence (II)

CTGGGCAAAATAAAATCAAATAG      (II)(SEQ ID NO:3).

The object of the invention is further achieved by a recombinant DNA, comprising a gene to be expressed which is different from the pfl gene; a promoter region upstream from said gene which contains a −35/−10 promoter sequence; a regulator region upstream from said promoter region which contains a sequence (I)(SEQ ID NO:4)

5'- ATGATCTATATCAA-3' or a 14 base pair sequence which is at least identical in 5 base pairs at positions 2, 3, 4, 11, 12 and 13 of said sequence (I), but wherein position 3 is not C, position 12 is not G and which is at least identical in a minimum of 2 base pairs, at positions 1, 5, 10 and 14 of said sequence (I). The recombinant DNA preferably also comprises a sequence which is at least 80% identical to the following consensus sequence: (SEQ ID NO:1)

```
        C  T
TATTTG  AT AA
        G  -
```

The regulator region preferably contains another sequence which is at least 50% identical to a sequence (II)

CTGGGCAAAATAAAATCAAATAG      (II)(SEQ ID NO:3).

More preferably, the regulator region of the present invention contains a sequence which is at least 65% identical to sequence (II).

The promoter sequence is preferably the lac, lambda $P_L$, trp or mgl promoter or is selected from the group consisting of (SEQ ID NO:5) AATGTAGGCTTAATGATTAGTCTGAGT-TATATTACGGGGCG;

(SEQ ID NO:6) TATCAATTTCTCATCTATAATGCTTTGT-TAGTATCTCGTCG;

(SEQ ID NO:7) TGGTATCCTGGCAAACCTGATGGTAT-GTCTGGCAGTATGGA;

(SEQ ID NO:8) GTTCATTATGGTGCTGCCGGTCGCGAT-GTTTGTTGCCAGCG;

(SEQ ID NO:9) CGGAATTTTGGACCGCAGTCGGTTCTG-CACCGGAAAATTTT;

(SEQ ID NO:10) CATTATCGGTGGTGGTTTGTTGGT-TGGGTTGACATACTGGG; and (SEQ ID NO:11) ACCACCATTAATGGTTGTCGAAGTACG-CAGTAAATAAAAAA.

More preferably, the promoter sequence is selected from the group consisting of:

(SEQ ID NO:5) AATGTAGGCTTAATGATTAGTCTGAGT-TATATTACGGGGCG; and (SEQ ID NO:6) TATCAATTTCTCATCTATAATGCTTTGT-TAGTATCTCGTCG.

Of considerably preference, the recombinant DNA of the present invention comprises a gene to be expressed which is different from the pfl gene and upstream thereof, the sequence shown in FIG. 10; and a promoter sequence, wherein said promoter sequence is lac, lambda $P_L$, trp, mgl or is selected from the group consisting of the following sequences:

(SEQ ID NO:5) AATGTAGGCTTAATGATTAGTCTGAGT-TATATTACGGGGCG;

(SEQ ID NO:6) TATCAATTTCTCATCTATAATGCTTTGT-TAGTATCTCGTCG;

(SEQ ID NO:7) TGGTATCCTGGCAAACCTGATGGTAT-GTCTGGCAGTATGGA;

(SEQ ID NO:8) GTTCATTATGGTGCTGCCGGTCGCGAT-GTTTGTTGCCAGCG;

(SEQ ID NO:9) CGGAATTTTGGACCGCAGTCGGTTCTG-CACCGGAAAATTTT;

(SEQ ID NO:10) CATTATCGGTGGTGGtTTGTTGGT-TGGGTTGACATACTGGG; and (SEQ ID NO:11) ACCACCATTAATGGTTGTCGAAGTACG-CAGTAAATAAAAAA.

With respect to the 23 base pair sequence and 14 base pair sequence as aforementioned, it is to be understood that deletions in the sequences are encompassed by the present invention resulting sequences being less than 23 or 14 base pairs.

A further embodiment of the invention is an expression vector which contains a recombinant DNA according to the present invention ligated into a suitable vector.

These DNA sequences of the recombinant DNA sequences according to the present invention are located in the expression vector, according to the present invention, upstream (i.e. on the 5' side) of the transcription start of the gene to be expressed which is controlled by this promoter whereby an ATG codon, and preferably also a Shine-Dalgarno sequence, is located between promoter and the gene which is to be expressed.

In a preferred embodiment of the invention the expression vector according to the present invention contains a polylinker or a single restriction cleavage site, i.e. a restriction cleavage site which is present only once in the expression vector, at the site at which the foreign gene to be expressed is to be inserted.

In a further preferred embodiment the PFL gene or parts of it and, if desired, untranslated upstream regions of the PFL gene which contain e.g. the ATG codon and the Shine-Dalgarno sequence, are present between the promoter region and the foreign gene to be expressed. It is particularly preferable to use the sequence shown in FIG. 10 for this, especially the entire sequence. In another preferred embodiment the expression vector contains the recombinant DNA according to the present invention, untranslated sequences of the upstream region of the PFL gene of FIG. 10 as well as the Shin-Dalgarno sequence and ATG of the foreign gene and, if desired, already the foreign gene itself. It is, however, also possible, according to the present invention, to couple the foreign gene including its start codon directly to the recombinant DNA according to the present invention.

A further embodiment of the invention is a process for the production of a recombinant DNA according to the present invention in which the PFL gene together with its upstream regions is isolated from the gene bank of a microorganism containing this gene, if desired, the parts which are not required are removed by well-known methods, and the desired sequences are combined with a promoter region or third sequences.

The ligation, restriction and deletion of DNA sequences is carried out according to the usual methods for this purpose.

In a preferred embodiment of the invention the DNA sequence is isolated from the gene bank of a microorganism of the *Enterobacteriaceae* family and preferably from *E.coli*.

Another further embodiment of the invention is a process for the production of an expression vector according to the present invention. For this, the recombinant DNA according to the present invention and, if desired, also a polylinker, a Shine-Dalgarno sequence, a start codon and/or further desired sequences are inserted into a suitable vector. Suitable vector molecules for this are known to the expert e.g. pBR322 or derivatives thereof.

The use, according to the present invention, of a recombinant DNA or expression vector as described above for the inducible and repressible expression of a foreign gene is characterized in that the induction is effected under anaerobic conditions and by pyruvate and the repression is effected by oxygen.

In this process the expression can be carried out in suitable microorganisms of the *Enterobacteriaceae* genus such as preferably *E.coli* and *Salmonella*, or other gram-negative bacteria such as preferably Pseudomonas, or in gram-positive bacteria.

The expression is preferably carried out in a host strain which is FNR-positive and which thus forms a functional FNR gene product. This is preferably *E.coli* FM 420 which is deposited at the German Collection for Microorganisms, DSM 5312.

The FNR protein (Stewart, V. Microbiol. Rev. 52 (1988) 190–232), which is produced by FNR-positive microorganisms, is a dimeric protein which can interact with the operator of the promoter according to the present invention and thus activates the expression.

It is of course possible to use a host strain which is FNR-negative; however, in this case the cell has to be supplied with the FNR protein in order to achieve an activation. For this purpose the FNR gene can be ligated into the expression vector according to the present invention which also carries or will carry the desired foreign gene and by this means expression of the FNR protein is achieved simultaneously with the expression of the foreign gene. The FNR gene can also be present in the host cells on an additional vector. In this case the production of the FNR protein is independent of the production of the foreign gene whereby this is however induced by the FNR protein. This embodiment i.e. the incorporation of at least one FNR gene on a separate vector is therefore preferred according to the present invention.

It is possible to regulate the expression of a foreign gene in a simple manner by the recombinant DNA according to the present invention. Thus, for example, an interfering expression of the foreign gene is suppressed in the aerobic early growth phase of the microorganism used. In the transition to the late logarithmic anaerobic growth phase, the expression is then induced by the pyruvate formed by the microorganism and an enhancement of the expression is achieved by the addition of pyruvate in the growth medium. A further simplification is that in the late anaerobic growth phase the cells are already fully grown and have reached an optimal density. In this case a limitation of oxygen automatically occurs which can be amplified or regulated by the fermentation technique. An optimal expression can be achieved by the high cell density of the microorganism.

A preferred process for the production of recombinant DNA, comprises isolating the DNA sequence shown in FIG. 10 or a substantial part thereof from a gene bank of a microorganism containing said sequence; and ligating said isolated sequence to a promoter sequence and a gene to be expressed, which is different from the pfl gene. The microorganism is preferably *E. coli*.

Another preferred process involves the inducible and repressible expression of a gene to be expressed which is different from the pfl gene and comprises the steps of inserting said gene to be expressed into an expression vector which comprises in a location upstream of said gene:

(i) a promoter region which contains a –35/–10 promoter sequence;

(ii) a regulator region which contains a sequence (I)(SEQ ID NO:2)

5'-GAGATATGATCTATATCAATTTC-3'        (I)

or a 23 base pair sequence which is at least 80% identical to position 6–10 and 15–19 of said sequence (I) but not having C at position 8 and/or G at position 17 and which is at least 80% identical to said sequence (I);

transforming a microbial host with said expression vector and culturing said host under conditions suitable to induce and repress expression of said gene to be expressed and obtaining said gene product.

The expression vector of the aforementioned process preferably further comprises a sequence which is at least 80% identical to the following consensus sequence:(SEQ ID NO:1)

```
      C  T
TATTTG AT AA.
      G  -
```

Preferably, the regulator region also contains a sequence which is at least 50% identical to a sequence (II)

CTGGGCAAAATAAAATCAAATAG        (II)(SEQ ID NO:3).

A further preferred process involves the inducible and repressible expression of a gene to be expressed which is different from the pfl gene and comprises the steps of:

inserting said gene to be expressed into an expression vector which comprises in a location upstream of said gene:

(i) a promoter region which contains a –35/–10 promoter sequence;

(ii) a regulator region which contains a sequence (I) (SEQ ID NO:4)

5'-ATGATCTATATCAA-3'        (I)

or a 14 base pair sequence which is at least identical in 5 base pairs at positions 2, 3, 4, 11, 12 and 13 of said sequence (I), but wherein position 3 is not C, position 12 is not G and which is at least identical in a minimum of 2 base pairs at positions 1, 5, 10 and 14 of said sequence (I);

transforming a microbial host with said expression vector and culturing said host under conditions suitable to induce and repress expression of said gene to be expressed and obtaining said gene product.

The expression vector of the above process preferably also comprises a sequence which is at least 80% identical to the following consensus sequence:(SEQ ID NO:1)

```
        C  T
TATTTG  AT AA
        G  -
``` and the regulator region may further contain a sequence which is at least 50% identical to a sequence (II)

CTGGGCAAAATAAAATCAAATAG  (II)(DEQ ID NO:3)

In the processes described wherein the host is first cultured under aerobic conditions thereby repressing expression of said gene to be expressed and later logarithmic growth phase induction of expression of said gene to be expressed is effected under anaerobic conditions and by pyruvate. The microbial host used in the process is preferably a gram- negative or gram-positive bacteria.

More preferably, the bacteria is *E. coli, Salmonella* or *Pseudomonas*.

The microbial host may also be FNR-positive, and it is preferred that such host be *E. coli* FM420. The microbial host may also be FNR-negative and the expression vector comprising a FNR gene. Therefore, the process of the present invention may include transforming the microbial host with an additional expression vector comprising the FNR gene, said microbial host being FNR-negative.

The use of the recombinant DNA and the expression vector according to the present invention for the production of proteins thus represents an inexpensive and simple alternative for the regulation since expensive and complicated inductions (addition of inducer, temperature shift etc.) are no longer necessary. The invention is further elucidated by the following Examples in conjunction with the Figures.

BRIEF DESCRIPTION OF THE DRAWINGS

The Figures show:

FIG. 1: A) Section from the plasmid p29: Complete regulatory region and pfl structural gene with the adjoining terminators. fnr: binding site for the fnr gene product; tr: transcription start; t: terminator. B) Section from the plasmid p29: The most important cleavage sites for restriction enzymes are marked.

B: BamHI; E: EcoRI; S: SalI; H: HindIII;

M: MluI;

P: PstI; Pv: PvuI.

Figure 9:
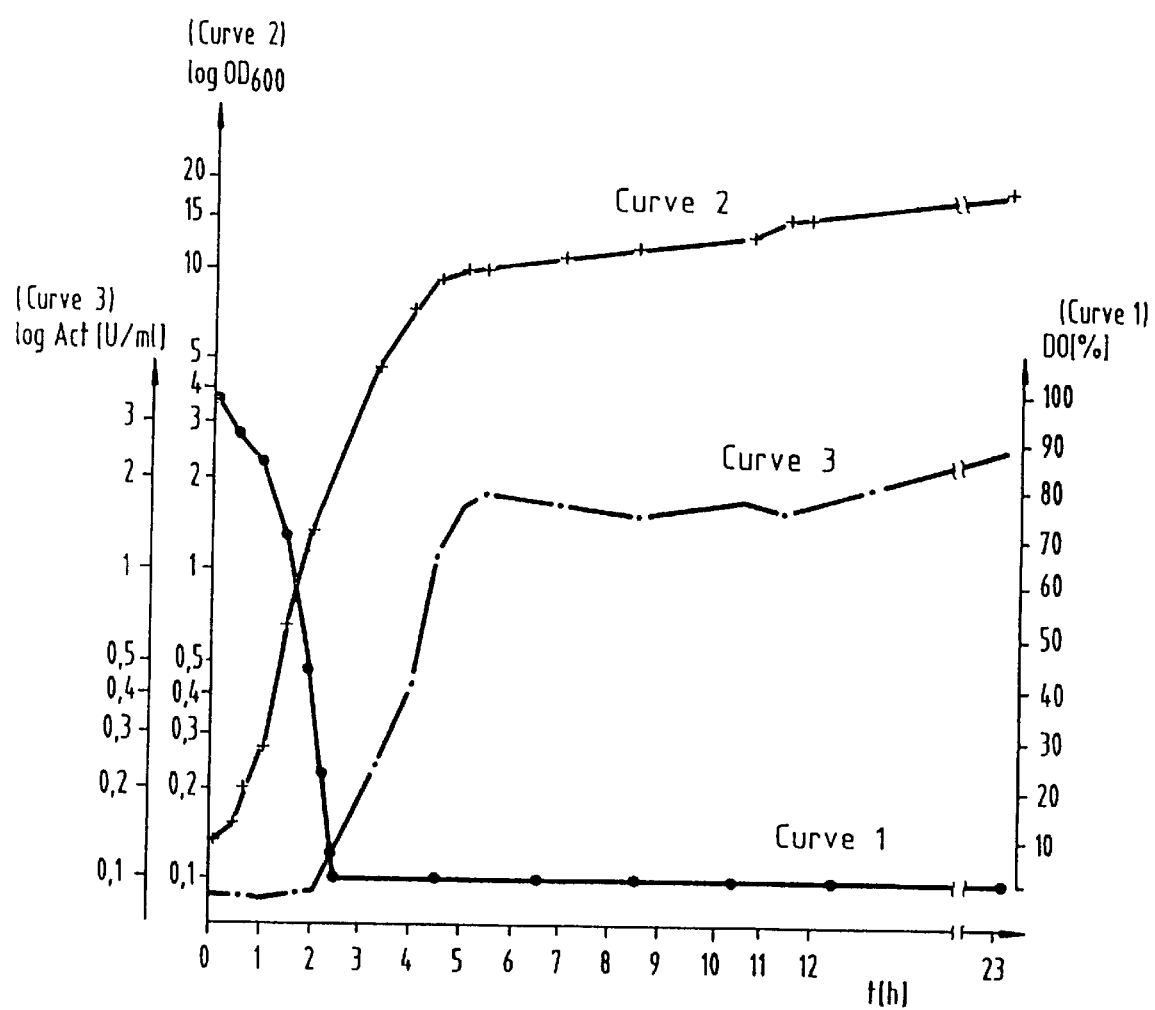

FIG. 9: Kinetics of a fermentation run: FM420 (PPFL23S-C). Fermenter: Bioflo II (New Brunswick); Filled volume:4.0 1; stirring rate: constant at 300 rpm; aeration: constant at 4.0 1/min; the curves show:

time-course of growth (cell density as log OD600);

expression of the creatinase gene at an increasing deficiency of oxygen (volume activity: log units/ml medium);

Decrease in the content of dissolved oxygen (%) during the course of the growth.

FIG. 10: Sequence of the pfl promoter region. The start codon of the pfl structural gene is underlined; the position of the first nucleotide (A of the ATG) is numbered +1.

FIG. 11: Promoter regions 1–7

GENERAL COMMENTS ON THE CONSTRUCTION OF THE EXPRESSION PLASMIDS

1.) All anaerobic cultures were carried out in serum flasks according to Balch W. E. and Wolfe R. S. (1976) Appl. Environ. Microbiol. 32:781–791. Aerobic cultures were carried out in Erlenmeyer flasks which were shaken vigorously (the flasks were filled to a maximum of ⅒ of their nominal volume). The cultures were incubated at 37° C.

2.) Medium: TGYEP (pH 6.5; 0.4 % glucose) (Begg Y. A., Whyte J. N., Haddock B. A. (1977) FEMS Microbiol. Lett. 2:47–50).

3.) Transformation of the strains used with plasmid DNA was carried out according to standard procedures (Maniatis T., Fritsch E. F., Sambrook (1982) Molecular cloning: a laboratory manual. Cold Spring Harbor Laboratory, Cold Spring Harbor N.Y.).

4.) Determination of t he pfl enzyme activity was carried out according to Conradt et al. (1984) Arch. Biochem. and Biophysics 228:133.

5.) Determination of the creatinase enzyme activity was carried out according to Schmitt J. (1984) Diplomarbeit, Univ. Wurzburg. The specific activity (U/mg protein) is quoted.

6.) Determination of the β-galactosidase enzyme activity was carried out according to Miller J. H. (1972) Experiments in molecular genetics. Cold Spring Harbor Laboratory, Cold Spring Harbor N.Y. The activities are quoted as Miller units.

7.) The integration of the pfl-lacZ fusion into the chromosome was carried out according to the method of Simons R. W., Houman F., Kleckner N. (1987) Gene 53:85–96. Starting with strain RM102 (fnr–, DSM 5311), the following transductants were obtained: RM135, RM136, RM409, RM415, RM412. Starting with strain FM420 (fnr+, DSM 5312), the following transductants were obtained: RM123, RM124, RM401, RM404, RM407.

Starting vectors:

1.) M13mp18 (Yanisch-Perron, Vieira, Messing (1985) Gene 33: 103–119)

2.) M13l11RX (Waye M. M. Y. et al. (1985) Nucleic Acids Res. 13: 8561–8571)

3.) pBT2a-1 (DSM 3148 P)

4.) p29 (Christiansen L., Pedersen S. (1981) Mol. Gen. Genet. 181: 548–551; DSM 5380)

The fusion of the promoter to the creatinase structural gene was carried out by directed deletion mutagenesis on the single-stranded DNA of a M13 construction. This contains a pfl fragment (regulatory sequence and the beginning of the structural gene), a selection marker for the mutagenesis (EcoK cassette: contains 4 times in sequence the recognition sequence for the restriction system K from *E.coli*) and a fragment of the creatinase gene (beginning of the structural gene with a part of the 5' untranslated sequence).

The plasmids p29 (Christiansen L., Pedersen S. (1981) Mol. Gen. Genet. 181:548–551; DSM 5380) pRS551 (DSM 5382), pRS552 (DSM 5381) (Simons R. W., Houman F., Kleckner N. (1987) Gene 53:85–96) were used for the pfl-lacZ fusions (Examples 8–12).

EXAMPLE 1

Cloning of the EcoK cassette and the creatinase fragment in M13mp18

Figure 2:
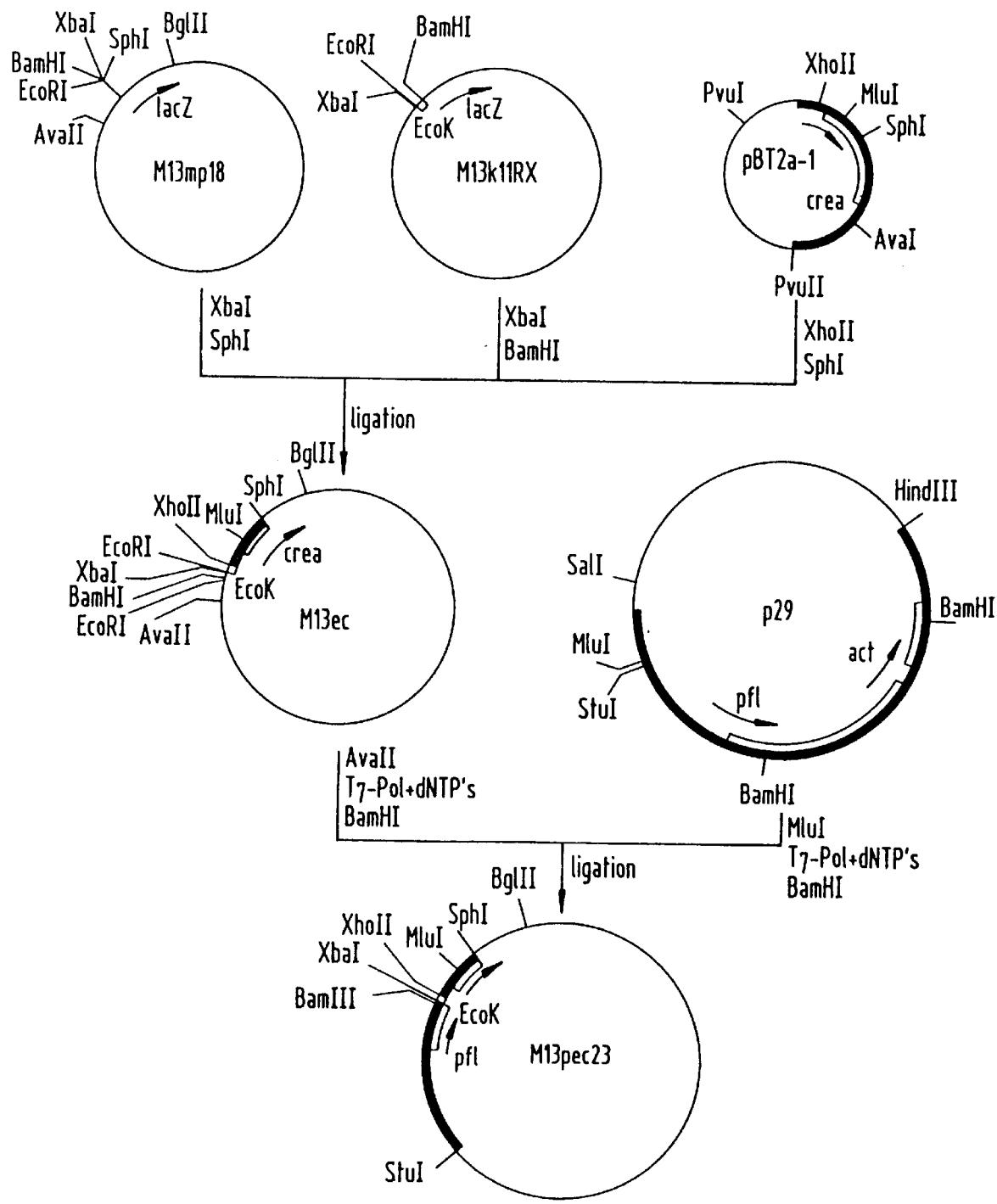
FIG. 2: Construction of the M13 derivative M13pec23. (Explanation in the text).

In preparation for the deletion mutagenesis, the individual components were cloned in M13mp18. In the first step, the EcoK cassette and the creatinase fragment were inserted into the XbaI/SphI cleaved vector. The EcoK cassette was isolated as a 90 bp XbaI/BamHI fragment from M13k11RX (Waye M. M. Y. et al. (1985) Nucleic Acids Res. 13:8561–8571). The creatinase fragment was isolated as a 580 bp XhoII/SphI fragment from pBT2a-1. It contains the first 460 nucleotides of the structural gene and 120 nucleotides of the 5' untranslated sequence. The 5' protruding end of the XhoII cleavage site is compatible with the protruding end of the BamHI cleavage site (EcoK cassette). EcoK cassette, creatinase fragment and vector were added together and ligated via the corresponding cleavage sites (FIG. 2). *E. coli* RR1dM15 (rk–, mk–; ATCC 35102) was transfected.

The construction which was obtained was denoted M13ec.

EXAMPLE 2

Cloning of the pfl promoter fragment in M13ec

The promoter region of the pfl gene was isolated as a 1786bp MluI/BamHI fragment from the plasmid p29 (pfl sequence: +390 to –1396, in relation to the first nucleotide of the pfl structural gene, A of the ATG of FIG. 10). p29 was cut with MluI, the 5' protruding end was filled in with T7 polymerase in the presence of all 4 dNTP's and then cut again with BamHI. The vector M13ec was first cut with AvaII, the protruding end was also filled in and then cut again with BamHI. The isolated pfl fragment was inserted in M13ec in a directed manner and the construction obtained was denoted M13pec23 (FIG. 2). *E. coli* RR1dM15 (rk–, mk–; ATCC 35102) was transfected. The orientation of the creatinase fragment in M13pec23 corresponds to the direction of transcription of the pfl promoter.

EXAMPLE 3

Deletion mutagenesis

Two deletion mutageneses were carried out using oligonucleotides (analogous to the method of Waye M. M. Y. et al. (1985) Nucleic Acids Res. 13:8561–8571) in order to fuse the creatinase structural gene to the promoter. One translational fusion (replacement of the pfl structural gene by the creatinase structural gene from the start codon onwards) and one transcriptional fusion (fusion of the creatinase gene with its own Shine-Dalgarno sequence (SD-sequence) to the promoter) were prepared.

These were denoted M13pc23A and M13pc23S (see Table 1).

TABLE 1

| Construction | Fusion | Fusion point[1] Promoter | Creatinase |
|---|---|---|---|
| M13pc23A | translational | –1 | +1 |
| M13pc23S | transcriptional | –12 | –14 |

[1]the numbering is relative to the respective structural gene whose first nucleotide (A) was numbered +1.

TABLE 2

Sequence of the oligonucleotide and the template after mutagenesis

| Construction | Start of Crea. with | Sequence | Oligonucleotide length (b) | bp deleted |
|---|---|---|---|---|
| M13pc23A | ATG | (SEQ ID NO: 12)<br>5'GAAGGTAGGTGTTAC—ATGCAAATGCCCAAG3'<br>3'CTTCCATCCACAATG—TACGTTTACGGGTTC5' | 30 | 609 |
| M13pc23S | SD | (SEQ ID NO: 13)<br>5'ATAAAAAATTCCACTTAAG—AAGGGTTCACCCCC3'<br>3'TATTTTTTAAGGTGAATTC—TTCCCAAGTGGCGG5' | 33 | 608 |

Figure 3:
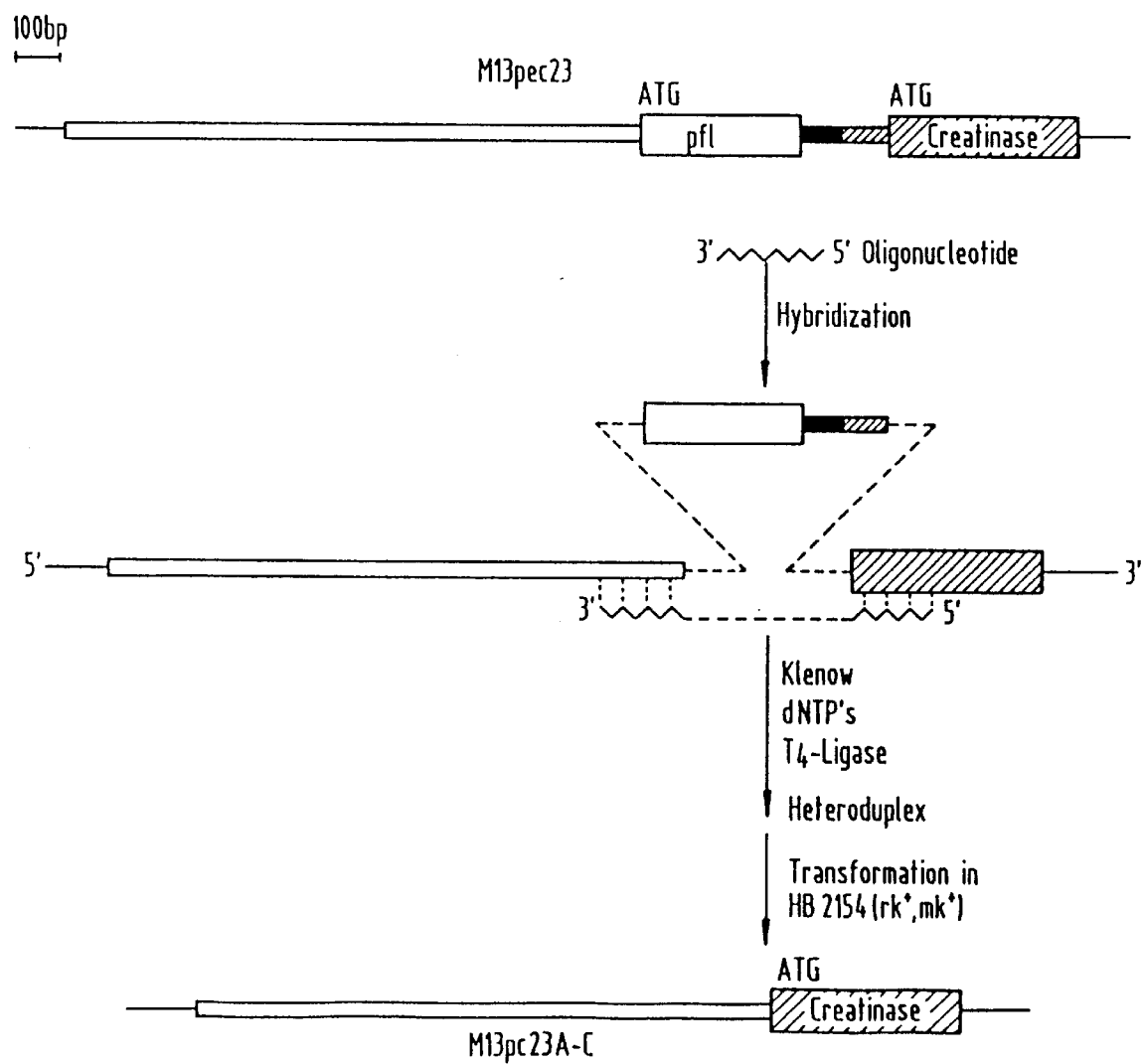
FIG. 3: Diagrams of the deletion mutagenesis for coupling the creatinase gene to the pfl promoter; shown for M13pec23S as an example. Creatinase sequences are shaded; the EcoK cassette is represented by the black bar. (Explanation in the text).
Figure 4:
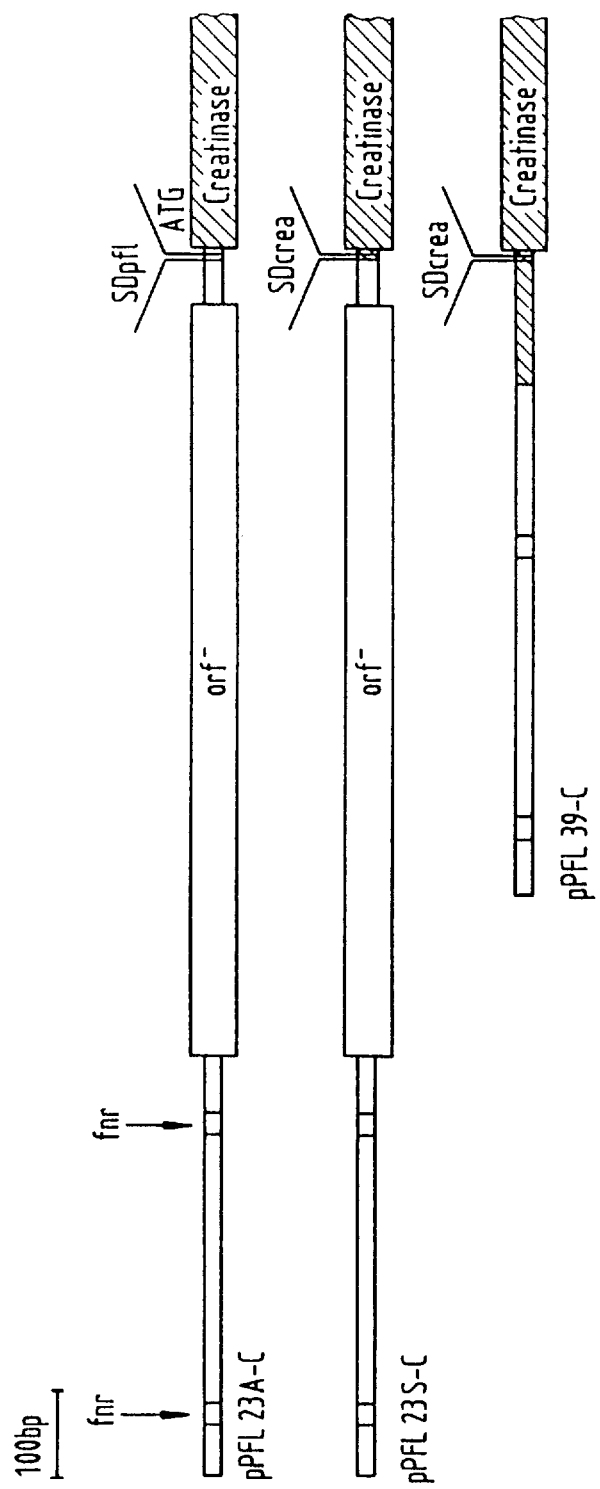
FIG. 4: Summary of the pfl-creatinase fusions: The diagrams each show a section from the plasmids pPFL23S-C, pPFL23A-C and pPFL39-C. SD: Shine-Dalgarno region.

Procedure for the mutagenesis: (see FIG. 3)

a) Hybridization of the mutagenic oligonucleotide to the M13 plus-strand. The DNA sequence to be deleted between the fusion points remains unpaired.

b) The remainder of the M13 single-stranded DNA is filled in to a double-strand with Klenow and dNTP's.

c) The selection against the non-mutated parent strand is carried out in vivo after transformation in *E.coli JM83* (rk+, mk+; ATCC 35607).

EXAMPLE 4

Directed mutagenesis in the orf gene

In order to prevent an over-expression of the orf gene product by the gene dose effect in the later expression vectors (high copy plasmids), two sequential stop codons were introduced into the reading frame of the orf gene by directed mutagenesis according to Kunkel (Kunkel T. (1985) Proc. Natl. Acad. Sci. 82:488–492; Kunkel T., Roberts J., Zakour R. (1987) Methods in Enzymol. 154:367–382).

The base substitutions were carried out with a mutagenic oligonucleotide on the plus-strand DNA of the construction M13pc23S. The substituted bases and their positions are shown in the following diagram:

```
5'...—...—AAC—TAG—TAA—...—...—...—...—...-3'
                 :    ::
(SEQ ID NO:14) 5'CG—AAA—AAC—TGG—CTA—AAT—GTC—TAT—TTT-3'

(SEQ ID NO:15)    3'—TTT—TTG—ATC—ATT—TTA—CAG—A5'
                                *
```

The middle strand corresponds to the sequence in the plus-strand of M13pc23S (5'→3'), the lower strand (3'→5') corresponds to that of the mutagenic oligonucleotide. The upper strand corresponds to the sequence after mutagenesis; the substituted bases are marked by colons (:). The asterisk marks the position −570 relative to the pfl structural gene.

No mutagenesis was carried out on the construction M13pc23A. In this case the pfl promoter region, including the intact orf gene, was removed via the cleavage sites AvaI and HindII and replaced by the corresponding segment from the orf mutant of M13pc23S.

EXAMPLE 5

Construction of the creatinase plasmid pGH-C without promoter

Starting vectors:

1.) pBTac1 (Boehringer Mannheim GmbH, Order No. 1081 365)

2.) pBT2a-1 pGH-C serves as the initial vector for the preparation of the expression vectors. This plasmid contains the complete creatinase structural gene and termination sequences; the expression cassette may be completed by recloning the fusions from the M13 derivatives into pGH-C.

a) Elimination of the tac promoter from pBTac1 In order to eliminate the tac promoter from pBTac1, the plasmid was cut with EcoRI and the 5' protruding end was filled in with T7 polymerase. Subsequently it was cut with PvuII and the vector part was isolated. The EcoRI cleavage site was regenerated by ligation of the blunt ends. The construction obtained was denoted pBTdtac.

b) Insertion of the creatinase gene in pBTdtac The creatinase gene was isolated from pBT2a-1. The plasmid was cut with AvaI and the fragment with the creatinase gene (ca. 1600bp) was isolated. The protruding ends were filled in and provided with BamHI linkers (BM). The fragment was inserted into the BamHI cleavage site of pBTdtac. The construction obtained was denoted pGH-C.

EXAMPLE 6

Recloning of the fusions from M13 into pGH-C

Figure 5:
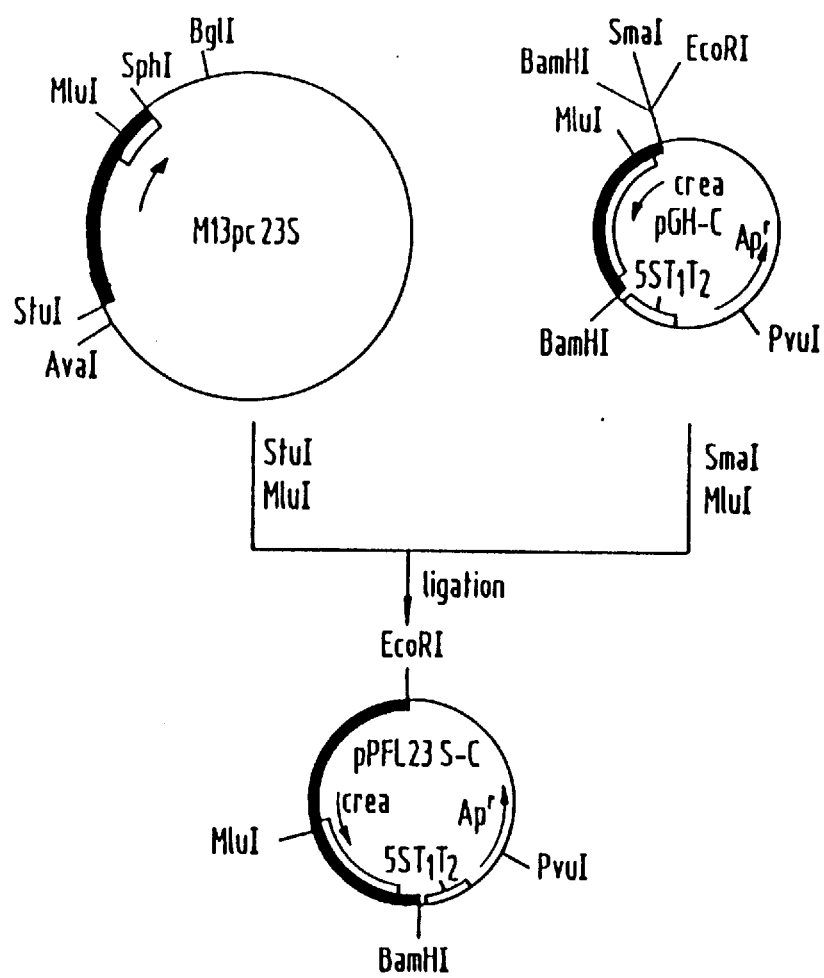
FIG. 5: Recloning of the the pfl-creatinase fusions from M13 in the plasmid pGH-C, shown for M13pc23S as an example.
Figure 6A:
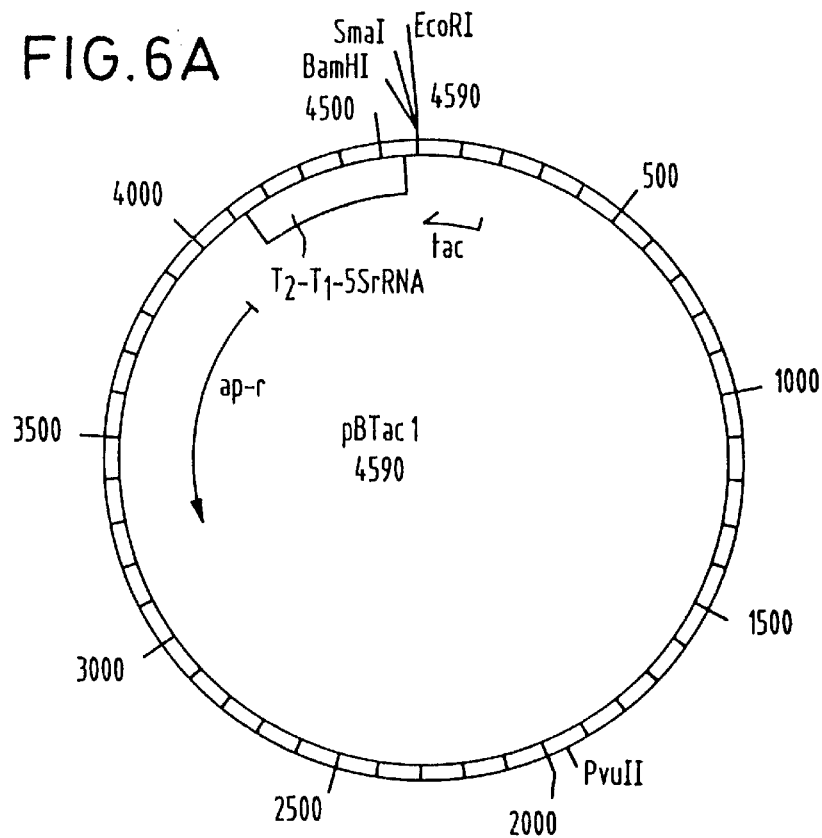
FIG. 6: A) Plasmid map of pBTac1 B) Plasmid map of pBT2a-1 C) Plasmid map of pBTdtac D) Plasmid map of pGH-C
Figure 6B:
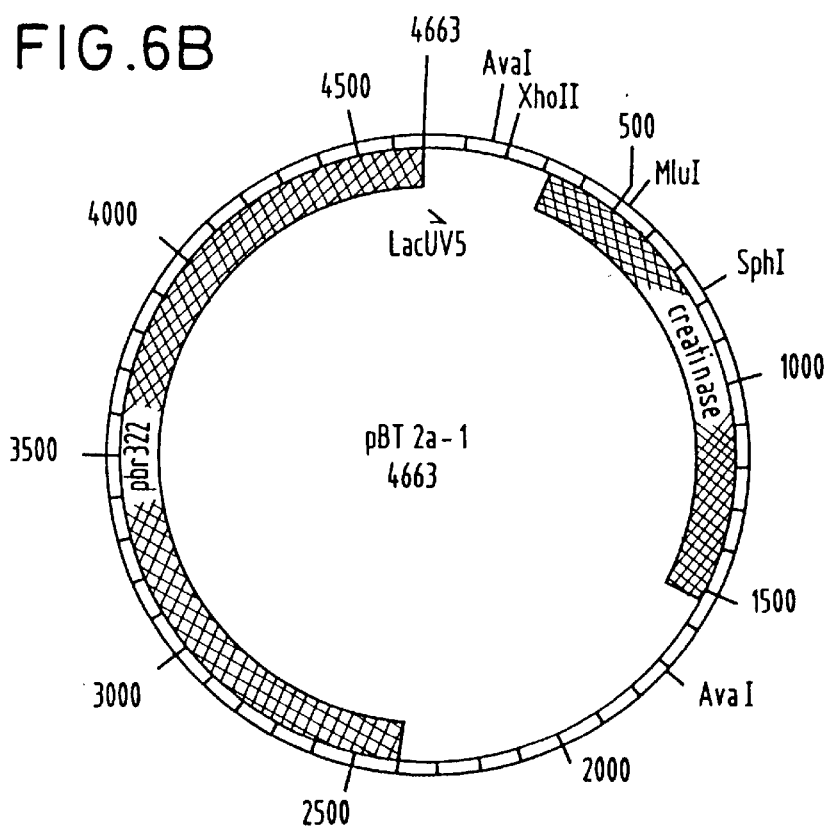
Figure 6C:
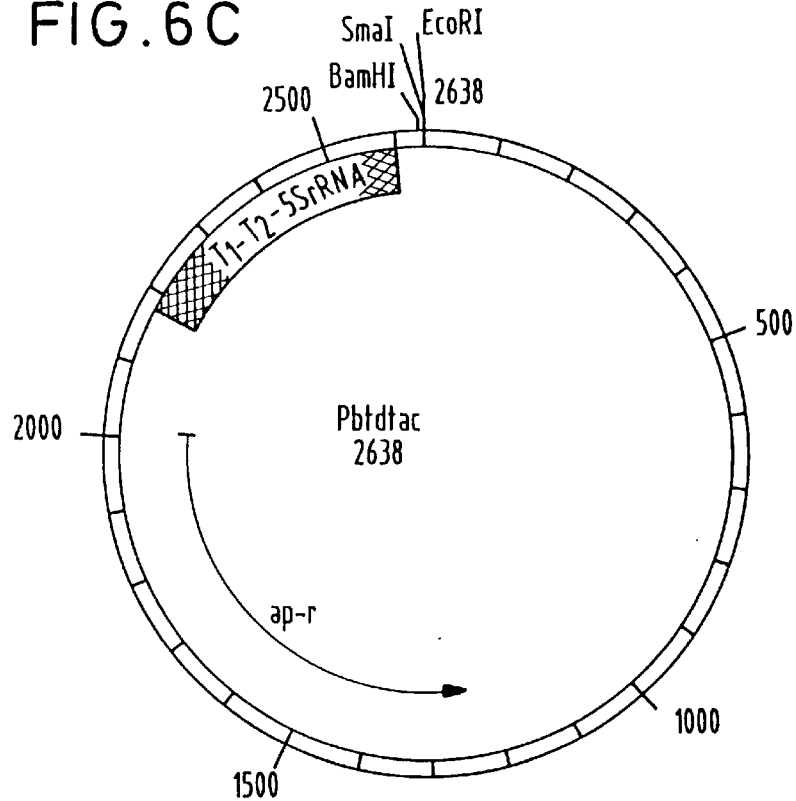
Figure 6D:
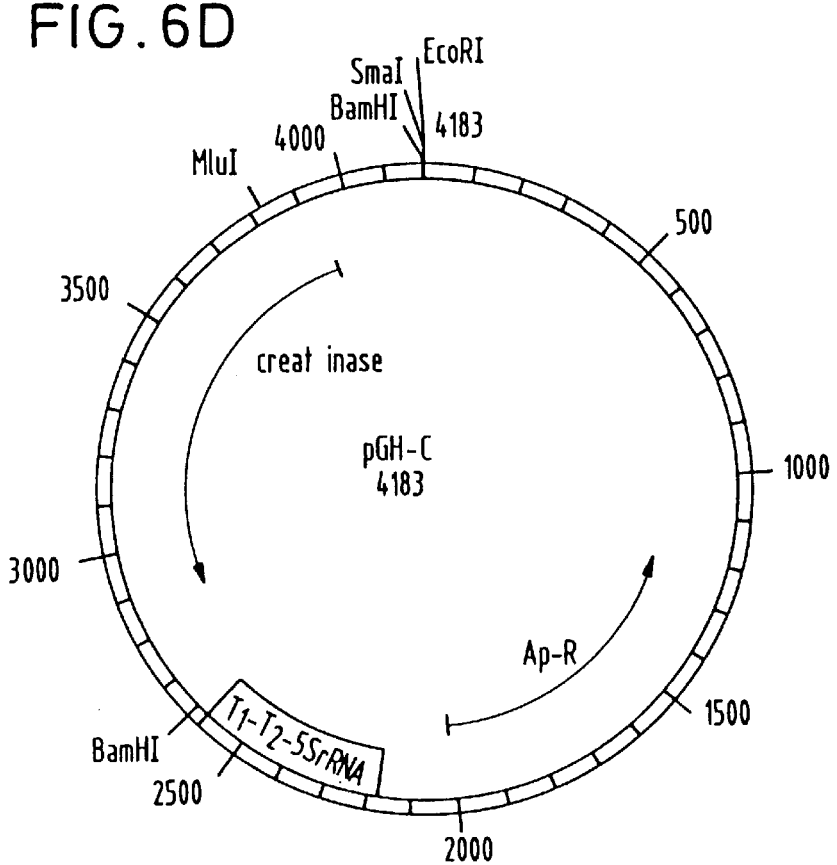
Figure 7A:
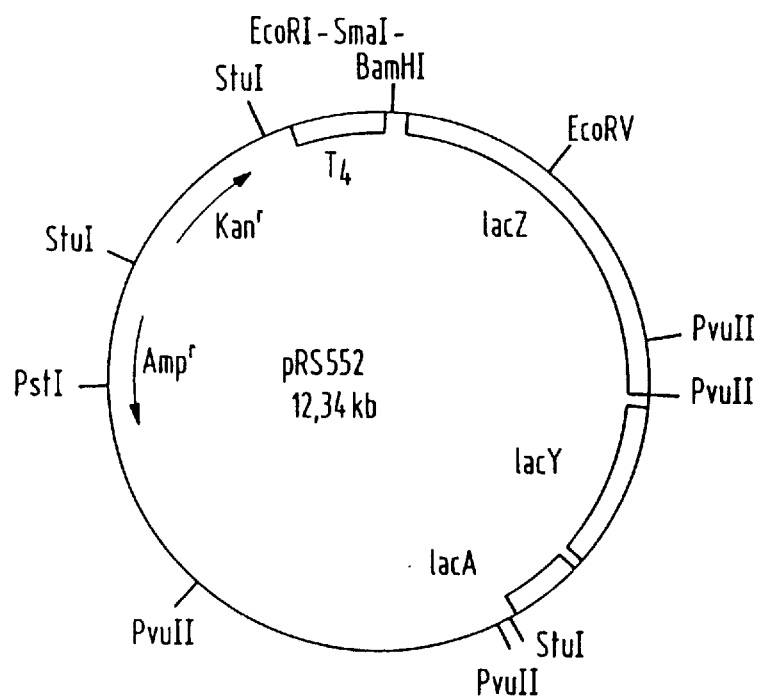
FIG. 7: A) Plasmid map of pRS552 B) Plasmid map of pRS551
Figure 7B:
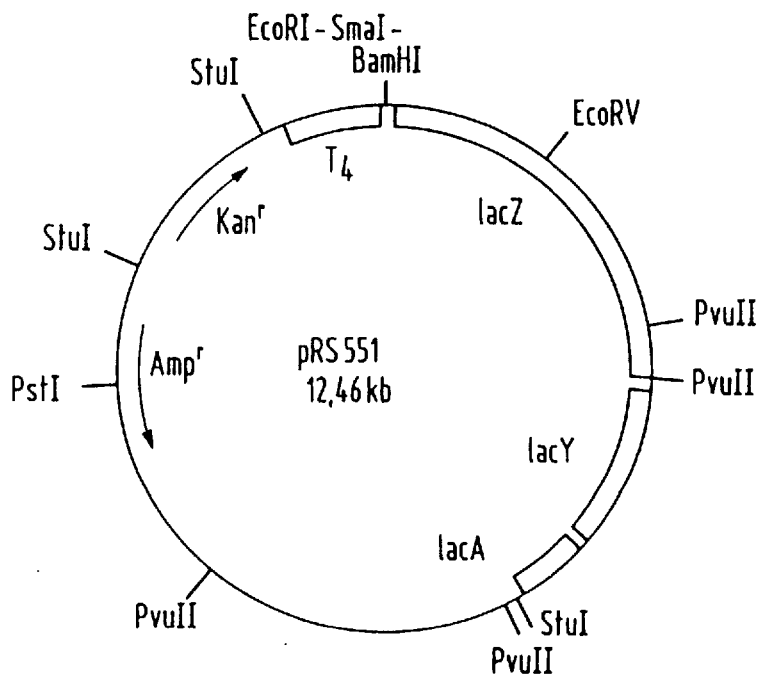

The fusion fragments from M13pc23S and M13pc23A were isolated via the cleavage sites StuI and MluI. The plasmid pGH-C was cut with SmaI and MluI and the vector part was isolated. The fusion fragments were inserted into the vector in such an orientation that the direction of transcription of the pfl promoter corresponds to the orientation of the creatinase gene (FIG. 5).

The expression plasmids were denoted pPFL23S-C and pPFL23A-C corresponding to the M13 construction. These vectors contain the following parts of the pfl promoter region:

| | |
|---|---|
| pPFL23A | Pos. −1 to −1364 inclusive |
| pPFL23S | Pos. −12 to −1364 inclusive |

EXAMPLE 7

Construction of the expression vector pPFL39-C

This plasmid contains only a shortened promoter element at the 5' end (promoters 6 and 7, fnr boxes 1 and 2; FIG. 1). This element corresponds to the 577 bp MluI/AflII fragment from p29 and contains the pfl sequence from position −819 to −1396 inclusive relative to the pfl start codon (A of the ATG=+1). The fragment was isolated via the EcoRI cleavage sites from the plasmid pRM39 (Example 10) and inserted into the EcoRI site of the plasmid PGH-C. The construction obtained was denoted pPFL-39C.

EXAMPLE 8

Construction of pRM23

Translational coupling of the complete promoter fragment with the lacz gene.

Figure 8:
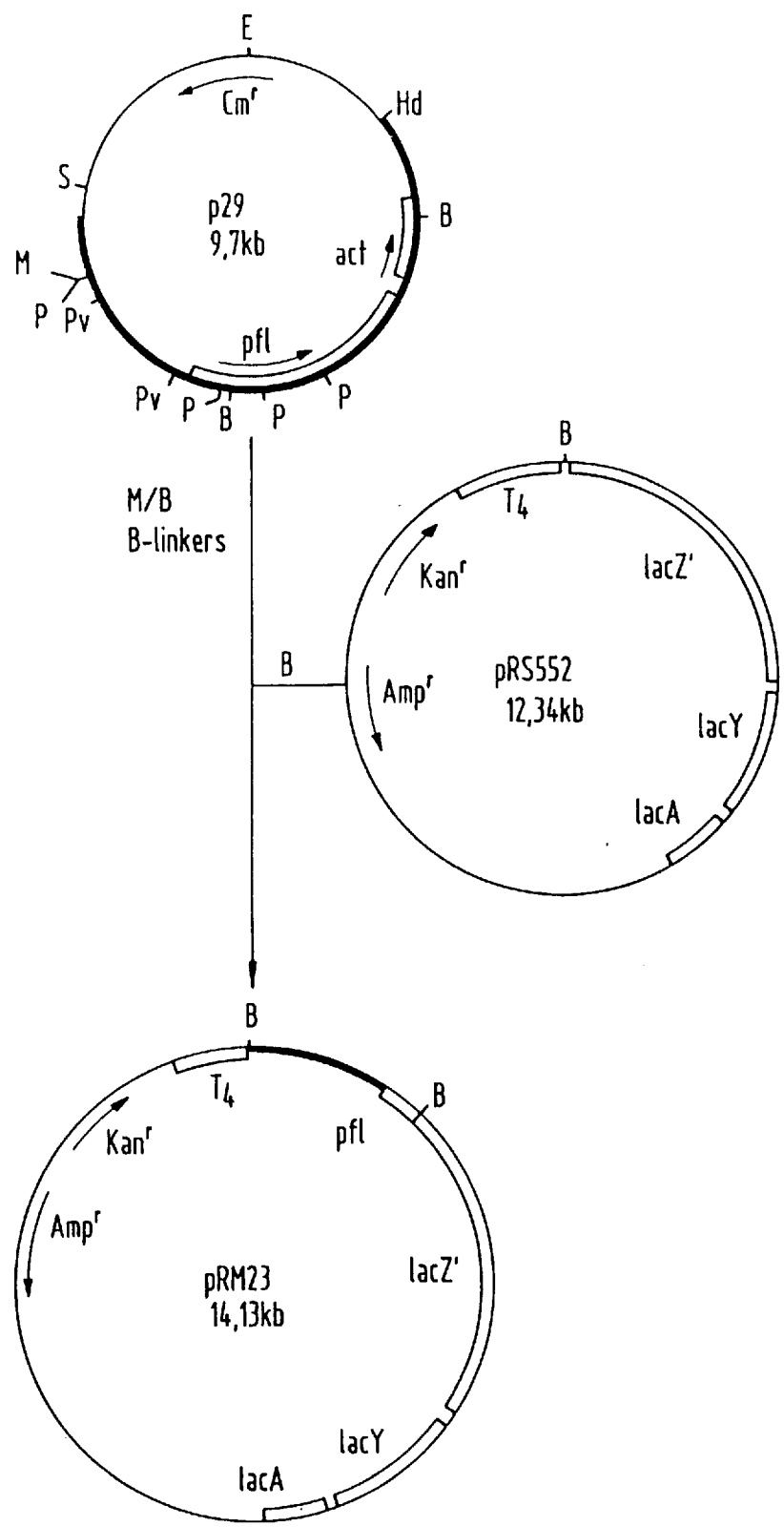
FIG. 8: Construction of plasmid pRM23: translational coupling of the complete pfl promoter fragment to lacZ.

For the isolation of the promoter fragment, p29 was cut with MluI and the protruding end was filled in with Klenow in the presence of all 4 dNTP's. Subsequently a BamHI linker (8-mer) was ligated on and cut with BamHI. The 1791bp fragment (including BamHI linker) was isolated and inserted into the BamHI cleavage site of pRS552 (FIG. 8).

The pfl fragment consists of the bases −1396 to +390 inclusive (relative to the first nucleotide of the pfl structural gene) and contains the promoters 1 to 7 and the fnr boxes 1 and 2.

EXAMPLE 9

Construction of pRM24

Translational coupling of a shortened promoter fragment with the lacZ gene.

The promoter element was isolated via the cleavage sites SspI and BamHI from p29 and inserted into pRS552 via the cleavage sites SmaI and BamHI. The pfl fragment consists of the bases −1045 to +390 inclusive (relative to the pfl start codon) and contains the promoters 1 to 7 and the fnr box 2.

EXAMPLE 10

Construction of pRM39

Transcriptional coupling of a shortened promoter fragment at the 5' end with the lacz gene.

The promoter element was isolated from p29 via the cleavage sites MluI and AflII, provided with EcoRI linkers (10-mer) and inserted into the EcoRI cleavage site of pRS551.

The pfl fragment consists of the bases −819 to −1396 inclusive (relative to the first nucleotide of the pfl structural gene) and contains the promoters 6 and 7 and the fnr boxes 1 and 2.

EXAMPLE 11

Construction of pRM43

Transcriptional coupling of a shortened promoter fragment at the 5' end with the lacZ gene.

The promoter element was isolated from p29 via the cleavage sites MluI and DraI, provided with EcoRI linkers (10-mer) and inserted into the EcoRI cleavage site of pRS551.

The pfl fragment consists of the bases −1075 to −1396 inclusive (relative to the first nucleotide of the pfl structural gene) and contains the promoter 7 and the fnr box 2.

EXAMPLE 12

Construction of pRM46

Transcriptional coupling of a shortened pfl fragment with the lacZ gene.

The promoter element was isolated from p29 via the cleavage sites NlaIII and BglI, provided with EcoRI linkers and inserted into the EcoRI cleavage site of pRS551.

The pfl fragment consists of the bases −861 to −1016 inclusive (relative to the first nucleotide of the pfl structural gene) and contains the promoter 6 and the fnr box 1.

EXAMPLE 13

Expression of pyruvate-formate lyase by the complete promoter fragment (promoter 1–7, fnr boxes 1 and 2): homologous expression.

The proportion of pyruvate-formate lyase is quoted in relation to the total cell protein under anaerobic conditions.

The determination was carried out by measuring the specific acitivity of the pyruvate-formate lyase formed.

|  | Strain: HB101 (free of plasmid) | Strain: HB101 (p29) |
|---|---|---|
| $-O_2$ [1] | 3% | ca. 30% |

[1] $-O_2$: under anaerobic conditions.

EXAMPLE 14

Expression of pyruvate-formate-lyase-β-galactosidase fusion protein by the complete promoter fragment (MluI-BamHI, promoters 1–7, fnr boxes 1 and 2): translational coupling.

|  | Strain: FM420 (pRM23) | Strain: RM123 (fnr+) | Strain: RM135 (fnr−) |
|---|---|---|---|
| $+O_2$ [2] | 10937 | 302 | 255 |
| $-O_2$ | >45000 | 4418 | 845 |
| $-O_2$, +Pyr. [3] | >45000 | 6642 | 869 |

[2] $+O_2$: under aerobic conditions
[3] +Pyr.: addition of 0.8% (w/v) pyruvate

EXAMPLE 15

Expression of pyruvate-formate-β-galactosidase fusion protein by the shortened promoter fragment (SspI-BamHI, promoters 1–6, fnr box 1): translational coupling.

|  | Strain: FM420 (pRM24) | Strain: RM124 (fnr+) | Strain: RM136 (fnr−) |
|---|---|---|---|
| $+O_2$ | 8993 | 217 | 389 |
| $-O_2$ | >45000 | 2669 | 610 |
| $-O_2$, +pyr. | >45000 | | |

EXAMPLE 16

Expression of β-galactosidase protein by the shortened promoter fragment (MluI-AflII, promoters 6–7, fnr boxes 1 and 2): transcriptional coupling.

|  | Strain: FM420 (pRM39) | Strain: RM401 (fnr+) | Strain: RM409 (fnr−) |
|---|---|---|---|
| $+O_2$ | 3441 | 203 | 439 |
| $-O_2$ | >38000 | 3238 | 1813 |
| $-O_2$, +pyr. | >45000 | | |

EXAMPLE 17

Expression of β-galactosidase protein by the shortened promoter fragment (MluI-DraI, promoter 7, fnr box 2): transcriptional coupling.

|  | Strain: FM420 (pRM43) | Strain: RM404 (fnr+) | Strain: RM412 (fnr−) |
|---|---|---|---|
| $+O_2$ | 220 | 7 | 6 |
| $-O_2$ | 1050 | 71 | 17 |

EXAMPLE 18

Expression of β-galactosidase protein by the shortened promoter fragment (NlaIII-BglI, promoter 6, fnr box 1): transcriptional coupling.

|  | Strain: FM420 (pRM46) | Strain: RM407 (fnr+) | Strain: RM415 (fnr−) |
|---|---|---|---|
| $+O_2$ | 11000 | 542 | 400 |
| $-O_2$ | >40000 | 3126 | 815 |
| $-O_2$, +pyr. | >40000 | | |

EXAMPLE 19

Expression of creatinase protein by the complete promoter fragment (promoters 1–7, fnr boxes 1 and 2): transcriptional coupling (region of translation initiation of the creatinase gene).

| | Strain:<br>JM83 (pPFL23S-C)[1] | Strain:<br>FM420 (pPFL23S-C)[2] |
|---|---|---|
| +O$_2$ | 0.008 | 0.181[3] |
| −O$_2$ | 0.050 | 1.476 |

[1] Cells harvested at OD600 = 0.5 (start to middle of the log phase).
[2] Cells harvested at OD600 = 4.0 (stationary growth phase).
[3] Creatinase enzyme activity: units/mg soluble protein.

Fermentation of FM420 (pPFL23S-C):

FIG. 9 shows the course of the creatinase expression (volume activity: units/ml) during the course of a fermentation process.

Fermenter: Bioflo II (New Brunswick, 5 litre fermenter)
Filled volume: 4 litres
Medium: K$_2$HPO$_4$ (3 H$_2$O):8 g/litre; KH$_2$PO$_4$ 2 g/litre Peptone: 10 g/litre; yeast extract (Ohly Kav): 32.4 g/litre; MgSO$_4$ (1M): 4 ml/litre; glucose: 0.4%.
Temperature: 32° C.
pH: 7.0 (constant)

The stirring rate (300 rpm) and the rate of aeration (4 l/min) were kept constant during the entire run.

Shown are:
growth curve (cell density expressed as OD600).
creatinase expression (units/ml).
content of dissolved oxygen (DO=dissolved oxygen; %).
It can be seen from the graph that:
The DO value is lowered as the cell density increases.
Growth is not influenced negatively when conditions of oxygen limitation occur (DO value=0).
Creatinase expression is induced at a low DO value.

EXAMPLE 20

Expression of creatinase protein by the complete promoter fragment (promoters 1–7, fnr boxes 1 and 2) with the region of translation initiation of the pfl gene (translational coupling).

| | Strain:<br>JM83 (pPFL23A-C) |
|---|---|
| +O$_2$ | 0.024 |
| −O$_2$ | 0.195 |

Cells were harvested in the stationary growth phase.

EXAMPLE 21

Expression of creatinase protein by the shortened promoter fragment (promoters 6 and 7, fnr boxes 1 and 2) with the region of translation initiation of the creatinase gene (transcriptional coupling).

| | Strain:<br>JM83 (pPFL39-C) |
|---|---|
| +O$_2$ | 0.006[4] |
| −O$_2$ | 0.045 |

[4] Cells were harvested at the beginning of the log phase.

EXAMPLE 22

A BamHI-fragment, 1786 bp in size, from pRM23 (Sawers, Böck (1988) J. Bacteriol. 170:5330–5336) was cloned in BamHI cut M13mp18 vector. By oligonucleotide directed mutagenesis according to Kunkel et al. (1987) Methods in Enzymology 154:367–382 two base substitutions were simultaneously inserted in the presumable FNR binding site 1 (upstream of promoter 6):

Oligonucleotide for the mutagenesis on FNR-binding site 1:

(SEQ ID NO:16) 5'-GAGATATCATCTATATGAATTTC-3'
                       G        C (wild type sequence)

In a second experiment two base substitutions were simultaneously inserted in the presumable FNR-binding site 2 (upstream of promoter 7):

Oligonucleotide for the mutagenesis on FNR-binding site 2:

(SEQ ID NO:17) 5'-GGGCAAAATAAAATGAGATAGC-3'
                        C   A (wild type sequence)

In a third experiment all four base substitutions were simultaneously inserted by using the two oligonucleotides described above.

The mutated 1786bp BamHI-fragments were in each case inserted in the vector pRS552 in replacement against the wild type sequence and transferred into the chromosome of E. coli FM102 (Simons et al. (1987) Gene). After aerobic and anaerobic growth in TGYHP pH 0.6% glucose (cf. Sawers, Böck (1988) J. Bacteriol. 170:5330–5336) the beta-galactosidase activity was determined.

| | Sequence of the FNR-Binding Sites in the pfl-Regulation Region | | | |
|---|---|---|---|---|
| Growth | Wild Type | FNR Box1 Mutant | FNR Box2 Mutant | Double-Mutant (Box1 + Box2) |
| aerobic | 250 | 243 | 239 | 160 |
| anaerobic | 5970 | 780 | 3807 | 677 |
| Growth | RM102 (fnr−) with Wild Type fl-Regulation Sequence | | | |
| aerobic | 256 | | | |
| anaerobic | 1045 | | | |

In each case the data indicate the beta-galactosidase activity according to Miller (1972) Experiments in Molecular Genetics. Cold Spring Harbor Laboratory, Cold Spring Harbor N.Y.

The data shows that a replacement of guanine and cytosine by their respective complimentary bases effects a strong reduction of anaerobic gene expression. Mutations in the binding site 2 (FNR Box 2 mutant), which corresponds to the region between −1308 and −1330 of the sequence shown in FIG. 10, does not show similar reduction of anaerobic expression of a heterologous gene.

We claim:

1. A recombinant DNA, comprising:

a gene to be expressed, wherein said gene is different from a pfl gene and is a foreign gene to any microorganism in which the gene is to be expressed;

a promoter region upstream from said gene to be expressed, wherein said promotor region contains a −35/−10 promoter sequence; and a regulator region, which regulates the expression of said gene, upstream from said promoter region, wherein said regulator region contains a sequence selected from the group consisting of:

5'-GAGATATGATCTATATCAATTTC-3'   (SEQ ID NO:2)

a 23 base pair sequence which is identical at positions 6–10 and 15–19 to SEQ ID NO:2, and

5'-GAGATATCATCTATATGAATTTC-3'   (SEQ ID NO:16)

2. The recombinant DNA according to claim 1, wherein said −35/−10 promoter sequence is identical to the following consensus sequence: (SEQ ID NO:1)

```
       C  T
TATTTG AT AA.
       G  -
```

3. The recombinant DNA according to claim 1, wherein said regulator region further comprises a sequence which is identical to a sequence (II)

(SEQ ID NO: 3) CTGGGCAAAATAAAATCAAATAG   (II)

operably linked to SEQ ID NO:2 or a 23 base pair sequence which is identical at positions 6–10 and 15–19 to SEQ ID NO:2 or SEQ ID NO:16.

4. The recombinant DNA according to claim 1, wherein said promoter sequence is selected from the group consisting of the lac, lambda $P_L$, trp and mgl promoters.

5. The recombinant DNA according to claim 1, wherein said promoter sequence is selected from the group consisting of

AATGTAGGCTTAATGATTAGTCTGAGTTATATTACGGGGCG (SEQ ID NO:5);

TATCAATTTCTCATCTATAATGCTTTGTTAGTATCTCGTCG (SEQ ID NO:6);

TGGTATCCTGGCAAACCTGATGGTATGTCTGGCAGTATGGA (SEQ ID NO:7);

GTTCATTATGGTGCTGCCGGTCGCGATGTTTGTTGCCAGCG (SEQ ID NO:8);

CGGAATTTTGGACCGCAGTCGGTTCTG-CACCGGAAAATTTT (SEQ ID NO:9);

CATTATCGGTGGTGGTTTGTTGGTTGGGTTGACATACTGGG (SEQ ID NO:10); and

ACCACCATTAATGGTTGTCGAAGTACG-CAGTAAATAAAAAA (SEQ ID NO:1 1).

6. The recombinant DNA according to claim 1, wherein said promoter sequence is selected from the group consisting of:

AATGTAGGCTTAATGATTAGTCTGAGTTATATTACGGGGCG (SEQ ID NO:5); and

TATCAATTTCTCATCTATAATGCTTTGTTAGTATCTCGTCG (SEQ ID NO:6).

7. A recombinant DNA, comprising:

a gene to be expressed wherein said gene is different from a pfl gene and is a foreign gene to any microorganism in which the gene is to be expressed;

a promoter region upstream from said gene to be expressed wherein said promotor region contains a −35/−10 promoter sequence;

a regulator region, which regulates the expression of said gene, upstream from said promoter region wherein said regulator region contains a sequence (III)

(SEQ ID NO:4) 5'-ATGATCTATATCAA-3'   (III)

or a 14 base pair sequence which is identical in at least 5 nucleotides at positions 2, 3, 4, 11, 12 and 13 to sequence (III), and wherein position 3 is not C, position 12 is not G and wherein at least 2 base pairs at positions 1, 5, 10 and 14 are identical to said sequence (III).

8. The recombinant DNA according to claim 7, wherein said −35/−10 promoter sequence is identical to the following consensus sequence: (SEQ ID NO:1)

```
              C  T
       TATTTG  AT  AA.
              G  -
```

9. The recombinant DNA according to claim 7, wherein said regulator region further comprises a sequence which is identical to sequence (II)

(SEQ ID NO:3) CTGGGCAAAATAAAATCAAATG   (II)

operably linked to SEQ ID NO:4 or a 14 base pair sequence which is identical in at least 5 nucleotides at positions 2, 3, 4, 11, 12 and 13 to sequence (III), and wherein position 3 is not C, position 12 is not G and wherein at least 2 base pairs at positions 1, 5, 10 and 14 are identical to said sequence (III).

10. A recombinant DNA comprising:

a gene to be expressed wherein said gene is different from a pfl gene and is a foreign gene to any microorganism in which the gene is to be expressed, the sequence shown in FIG. 10 (SEQ ID NO:18) upstream from said gene to be expressed; and a promoter sequence upstream from said sequence shown in FIG. 10, wherein said promoter sequence is selected from the group consisting of lac, lambda $P_L$, trp, mgl,

AATGTAGGCTTAATGATTAGTCTGAGTTATATTACGGGGCG (SEQ ID NO:5);

TATCAATTTCTCATCTATAATGCTTTGTTAGTATCTCGTCG (SEQ ID NO:6);

TGGTATCCTGGCAAACCTGATGGTATGTCTGGCAGTATGGA (SEQ ID NO:7);

GTTCATTATGGTGCTGCCGGTCGCGATGTTTGTTGCCAGCG (SEQ ID NO:8);

CGGAATTTTGGACCGCAGTCGGTTCTG-CACCGGAAAATTTT (SEQ ID NO:9);

CATTATCGGTGGTGGTTTGTTGGTTGGGTTGACATACTGGG (SEQ ID NO:10); and

ACCACCATTAATGGTTGTCGAAGTACG-CAGTAAATAAAAAA (SEQ ID NO:11).

11. An expression vector, comprising a gene to be expressed, wherein said gene is different from a pfl gene and is a foreign gene to any microorganism in which the gene is to be expressed;

a promoter region upstream from said gene to be expressed, wherein said promotor region contains a −35/−10 promoter sequence; and a regulator region, which regulates the expression of said gene upstream from said promoter region, wherein said regulator region contains a sequence selected from the group consisting of:

5'-GAGATATGATCTATATCAATTTC-3'(SEQ ID NO:2), a 23 base pair sequence which is identical at positions 6–10 and 15–19 to SEQ ID NO:2, and

5'-GAGATATCATCTATATGAATTTC-3'(SEQ ID NO:16).

12. The expression vector according to claim 11, further comprising a polylinker or a single restriction cleavage site in which the gene to be expressed is inserted.

13. The expression vector according to claim 11, further comprising a Shine-Dalgarno sequence, wherein said Shine-Dalgbarno sequence is situated between the gene to be expressed and the regulator and promoter regions.

14. The expression vector according to claim 11, further comprising at least a part of SEQ ID NO:18 as shown in FIG. 10 upstream from said gene to be expressed.

15. The expression vector according to claim 11, further comprising a start codon of a pfl gene, wherein said start codon is situated between the gene to be expressed and the upstream regulator and promoter sequences.

16. The expression vector according to claim 11, further comprising at least a part of SEQ ID NO:18 as shown in FIG. 10, wherein said part of SEQ ID NO:18 is situated between the gene to be expressed and the upstream regulator and promoter sequences.

17. An expression vector, comprising a gene to be expressed wherein said gene is different from a pfl gene and is a foreign gene to any microorganism in which the gene is to be expressed, the sequence shown in FIG. 10 upstream from said gene to be expressed; and a promoter sequence upstream from said sequence shown in FIG. 10, wherein said promoter sequence is selected from the group consisting of lac, lambda $P_L$, trp, mgl,

AATGTAGGCTTAATGATTAGTCTGAGTTATATTACGGGGCG (SEQ ID NO:5);

TATCAATTTCTCATCTATAATGCTTTGTTAGTATCTCGTCG (SEQ ID NO:6);

TGGTATCCTGGCAAACCTGATGGTATGTCTGGCAGTATGGA (SEQ ID NO:7);

GTTCATTATGGTGCTGCCGGTCGCGATGTTTGTTGCCAGCG (SEQ ID NO:8);

CGGAATTTTGGACCGCAGTCGGTTCTG-CACCGGAAAATTTT (SEQ ID NO:9);

CATTATCGGTGGTGGTTTGTTGGTTGGGTTGACATACTGGG (SEQ ID NO:10); and

ACCACCATTAATGGTTGTCGAAGTACG-CAGTAAATAAAAAA (SEQ ID NO:11).

18. A process for the inducible and repressible expression of a gene which is different from the pfl gene, comprising the steps of:

a) inserting said gene to be expressed into an expression vector downstream of:
   (i) a promoter region which contains a −35/−10 promoter sequence; and
   (ii) a regulator region, which regulates the expression of said gene upstream from said promotor region and which contains a sequence selected from the group consisting of:

(SEQ ID NO:2) 5'-GAGATATGATCTATATCAATTTC-3', a 23 base pair sequence which is identical at positions 6–10 and 15–19 to SEQ ID NO:2, and

5'-GAGATATCATCTATATGAATTTC-3'(SEQ ID NO:16), wherein said gene is a foreign gene to any microorganism in which the gene is to be expressed;

b) transforming a microbial host which is FNR positive and in which said promotor sequence is operable with said expression vector;

c) culturing said host under conditions wherein said gene to be expressed is repressed and induced, and d) isolating the gene product produced.

19. The process according to claim 18, wherein said −35/−10 promoter sequence is identical to the following consensus sequence: (SEQ ID NO:1)

```
       C  T
TATTTG AT AA.
       G  -
```

20. The process according to claim 18, wherein said regulator region further contains a sequence which is identical to a sequence (II)

(SEQ ID NO:3) CTGGGCAAAATAAAATCAAATAG     (II)

operably linked to SEQ ID NO:2 or a 23 base pair sequence which is identical at positions 6–10 and 15–19 to SEQ ID NO:2 or SEQ ID NO:16.

21. The process according to claim 18, wherein said suitable microbial host is selected from the group consisting of *E. coli*, *Salmonella* and *Pseudomonas*.

22. The process according to claim 18, wherein said host is first cultured under aerobic conditions thereby repressing expression of said gene to be expressed.

23. The process according to claim 18, wherein a later logarithmic growth phase, induction of expression of said gene to be expressed is effected under anaerobic conditions in the presence of pyruvate.

24. The process according to claim 18, wherein said microbial host is a gram-negative or gram-positive bacteria.

25. The process according to claim 18, wherein said microbial host is *E. coli* FM420.

26. The process according to claim 18, wherein said microbial host is selected from the group consisting of *E. coli*, *Salmonella* and *Pseudomonas*.

27. A process for the inducible and repressible expression of a gene to be expressed which is different from the pfl gene, comprising the steps of:
 a) inserting said gene to be expressed into an expression vector downstream from:
  (i) a promoter region which contains a −35/−10 promoter; and
  (ii) a regulator region, which regulates the expression of said gene, and which contains a sequence (III)

(SEQ ID NO:4) 5'-ATGATCTATATCAA-3'     (III)

or a 14 base pair sequence which is at least identical in 5 base pairs at positions 2, 3, 4, 11, 12 and 13 of said sequence (III), but wherein position 3 is not C, position 12 is not G and which is at least identical in a minimum of 2 base pairs at positions 1, 5, 10 and 14 of said sequence (III) wherein said gene is a foreign gene to any microorganism in which the gene is to be expressed; upstream of said promotor region,
 b) transforming a microbial host which is FNR positive and in which said promotor sequence is operable with said expression vector;
 c) culturing said host under conditions wherein said gene to be expressed is repressed and induced, and
 d) isolating the gene product produced.

28. The process according to claim 27, wherein said −35/−10 promoter sequence is identical to the following consensus sequence: (SEQ ID NO:1)

```
       C  T
TATTTG AT AA.
       G  -
```

29. The process according to claim 27, wherein said regulator region further contains a sequence which is identical to a sequence (II)

(SEQ ID NO:3) CTGGGCAAAATAAAATCAAATAG     (II)

operably linked to SEQ ID NO:4 or a 14 base pair sequence which is at least identical in 5 base pairs at positions 2, 3, 4, 11, 12 and 13 of said sequence (III), but wherein position 3 is not C, position 12 is not G and which is at least identical in a minimum of 2 base pairs at positions 1, 5, 10 and 14 of said sequence (III).

30. A process for the inducible and repressible expression of a gene which is different from the pfl gene, comprising the steps of:
 a) inserting said gene to be expressed into an expression vector downstream of:
  (i) a promoter region which contains a −35/−10 promoter sequence; and
  (ii) a regulator region which regulates the expression of said gene, upstream from said promotor region, and which contains a sequence selected from the group consisting of:

5'-GAGATATGATCTATATCAATTTC-3'(SEQ ID NO:2), a 23 base pair sequence which is identical at positions 6–10 and 15–19 to SEQ ID NO:2, and

5'-GAGATATCATCTATATGAATTTC-3'(SEQ ID NO:16);

b) inserting an FNR gene downstream of said gene to be expressed,
 c) transforming a microbial host which is FNR-negative and in which said promotor sequence is operable with said expression vector;
 d) culturing said host under conditions wherein said gene to be expressed is repressed and induced, and
 e) isolating any gene product produced.

31. A process for the inducible and repressible expression of a gene which is different from the pfl gene, comprising the steps of:
 a) inserting said gene to be expressed into an expression vector downstream of:
  (i) a promoter region which contains a −35/−10 promoter sequence; and
  (ii) a regulator region which regulates the expression of said gene upstream from said promotor region and which contains a sequence selected from the group consisting of:

5'-GAGATATGATCTATATCAATTTC-3'(SEQ ID NO:2), a 23 base pair sequence which is identical at positions 6–10 and 15–19 to SEQ ID NO:2, and

5'-GAGATATCATCTATATGAATTTC -3'(SEQ ID NO:16);

b) transforming a microbial host which is FNR-negative and in which said promotor sequence is operable with said expression vector;
 c) transforming said microbial host with an additional expression vector comprising an FNR gene;
 d) culturing said host under conditions wherein said gene to be expressed is repressed and induced; and
 e) isolating any gene product produced.

* * * * *

UNITED STATES PATENT AND TRADEMARK OFFICE
CERTIFICATE OF CORRECTION

PATENT NO. : 5,830,720

DATED : November 3, 1998

INVENTOR(S) : Böck et al.

It is certified that error appears in the above-identified patent and that said Letters Patent is hereby corrected as shown below:

TITLE PAGE:

Item [75], delete lines 1-4, insert therefor -- August Böck, Geltendorf, Germany; Robert Gary Sawers, Norwich, United Kingdom; Michael Jarsch, Bad Heilbrunn, Germany; Ronald Herbst, Menlo Park, California Signed and Sealed this Sixteenth Day of March, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: misc_feature
      ( B ) LOCATION: 10
      ( D ) OTHER INFORMATION: /note= "T in position 10 may be
         deleted."

( x i ) SEQUENCE DESCRIPTION: SEQ ID NO:1:

TATTTGSATT AA                                                                    12

( 2 ) INFORMATION FOR SEQ ID NO:2:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

GAGATATGAT CTATATCAAT TTC                                                        23

( 2 ) INFORMATION FOR SEQ ID NO:3:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:3:

CTGGGCAAA ATAAAATCAA ATAG                                                        23

( 2 ) INFORMATION FOR SEQ ID NO:4:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:4:

ATGATCTATA TCAA                                                                  14

( 2 ) INFORMATION FOR SEQ ID NO:5:

( i ) SEQUENCE CHARACTERISTICS:
      ( A ) LENGTH: 41 base pairs
      ( B ) TYPE: nucleic acid
      ( C ) STRANDEDNESS: single -continued (D) TOPOLOGY: linear (ii) MOLECULE TYPE: DNA (xi) SEQUENCE DESCRIPTION: SEQ ID NO:5:

AATGTAGGCT TAATGATTAG TCTGAGTTAT ATTACGGGGC G　　　　　　　　　　　　41

(2) INFORMATION FOR SEQ ID NO:6:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:6:

TATCAATTTC TCATCTATAA TGCTTTGTTA GTATCTCGTC G　　　　　　　　　　　　41

(2) INFORMATION FOR SEQ ID NO:7:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:7:

TGGTATCCTG GCAAACCTGA TGGTATGTCT GGCAGTATGG A　　　　　　　　　　　　41

(2) INFORMATION FOR SEQ ID NO:8:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:8:

GTTCATTATG GTGCTGCCGG TCGCGATGTT TGTTGCCAGC G　　　　　　　　　　　　41

(2) INFORMATION FOR SEQ ID NO:9:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:9:

CGGAATTTTG GACCGCAGTC GGTTCTGCAC CGGAAAATTT T　　　　　　　　　　　　41

(2) INFORMATION FOR SEQ ID NO:10:

(i) SEQUENCE CHARACTERISTICS:
                (A) LENGTH: 41 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:10:

CATTATCGGT GGTGGTTTGT TGGTTGGGTT GACATACTGG G                41

( 2 ) INFORMATION FOR SEQ ID NO:11:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

ACCACCATTA ATGGTTGTCG AAGTACGCAG TAAATAAAAA A                41

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:12:

GAAGGTAGGT GTTACATGCA AATGCCCAAG                              30

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:13:

ATAAAAAATT CCACTTAAGA AGGGTTCACC GCC                          33

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CGAAAAACTG GCTAAATGCT TATTTT                                  26

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

TTTTTGATCA TTTTACAGA                                          19

( 2 ) INFORMATION FOR SEQ ID NO:16:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:16:

GAGATATSAT CTATATSAAT TTC  23

( 2 ) INFORMATION FOR SEQ ID NO:17:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:17:

GGGCAAAATA AAATGMGATA GC  22

( 2 ) INFORMATION FOR SEQ ID NO:18:

( i ) SEQUENCE CHARACTERISTICS:
  ( A ) LENGTH: 1792 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:18:

| | | | | | | |
|---|---|---|---|---|---|---|
| ACGCGTTTGC | TGCACATCAG | TCGTTGTTGA | AGGCCTACGA | AAAGCTGCAG | CGCGCCAAAG | 60 |
| CAGCATTCTG | GGCAAAATAA | AATCAAATAG | CCTACGCAAT | GTAGGCTTAA | TGATTAGTCT | 120 |
| GAGTTATATT | ACGGGGCGTT | TTTTAATGC | CCCGCTTTAC | ATATATTTGC | ATTAATAAAA | 180 |
| TAATTGTAAT | TATAAGGTTA | AATATCGGTA | ATTTGTATTT | AATAAATACG | ATCGATATTG | 240 |
| TTACTTTATT | CGCCTGATGC | TCCCTTTTAA | TTAACTGTTT | TAGCGGAGGA | TGCGGAAAAA | 300 |
| ATTCAACTCA | TTTGTTAATT | TTTAAAATTT | ATTTTTATTT | GGATAATCAA | ATATTTACTC | 360 |
| CGTATTTGCA | TAAAAACCAT | GCGAGTTACG | GGCCTATAAG | CCAGGCGAGA | TATGATCTAT | 420 |
| ATCAATTTCT | CATCTATAAT | GCTTTGTTAG | TATCTCGTCG | CCGACTTAAT | AAAGAGAGAG | 480 |
| TTAGTGTGAA | AGCTGACAAC | CCTTTTGATC | TTTTACTTCC | TGCTGCAATG | GCCAAAGTGG | 540 |
| CCGAAGAGGC | GGGTGTCTAT | AAAGCAACGA | AACATCCGCT | TAAGACTTTC | TATCTGGCGA | 600 |
| TTACCGCCGG | TGTTTTCATC | TCAATCGCAT | TCGTCTTCTA | TATCACAGCA | ACCACTGGCA | 660 |
| CAGGCACAAT | GCCCTTCGGC | ATGGCAAAAC | TGGTTGGCGG | CATTTGCTTC | TCTCTGGGGC | 720 |
| TGATTCTTTG | TGTTGTCTGC | GGAGCCGATC | TCTTTACTTC | CACCGTGTTG | ATTGTTGTTG | 780 |
| CTAAGGCGAG | TGGGCGCATC | ACCTGGGGTC | AGTGGCGAA | AAACTGGCTA | AATGTCTATT | 840 |
| TTGGCAACCT | GGTCGGCGCA | CTGCTGTTTG | TACTTTTAAT | GTGGCTTTCC | GGCGAGTATA | 900 |
| TGACCGCAAA | TGGTCAATGG | GGACTAAACG | TCCTACAAAC | CGCCGACCAC | AAAGTGCACC | 960 |
| ATACTTTTAT | TGAGGCCGTC | TGTCTTGGTA | TCCTGGCAAA | CCTGATGGTA | TGTCTGGCAG | 1020 |
| TATGGATGAG | TTATTCTGGC | CGCAGCCTGA | TGGACAAAGC | GTTCATTATG | GTGCTGCCGG | 1080 |
| TCGCGATGTT | TGTTGCCAGC | GGTTTTGAGC | ACAGTATCGC | AAACATGTTT | ATGATCCCGA | 1140 |
| TGGGTATTGT | AATCCGCGAC | TTCGCATCCC | CGGAATTTTG | GACCGCAGTC | GGTTCTGCAC | 1200 |

-continued

| | | | | | | |
|---|---|---|---|---|---|---|
| CGGAAAATTT | TTCTCACCTG | ACCGTGATGA | ATTTCATCAC | TGATAACCTG | ATTCCGGTTA | 1260 |
| CGATCGGCAA | CATTATCGGT | GGTGGTTTGT | TGGTTGGGTT | GACATACTGG | GTCATTTACC | 1320 |
| TGCGTGAAAA | CGACCACCAT | TAATGGTTGT | CGAAGTACGC | AGTAAATAAA | AAATCCACTT | 1380 |
| AAGAAGGTAG | GTGTTACATG | TCCGAGCTTA | ATGAAAAGTT | AGCCACAGCC | TGGGAAGGTT | 1440 |
| TTACCAAAGG | TGACTGGCAG | AATGAAGTAA | ACGTCCGTGA | CTTCATTCAG | AAAAACTACA | 1500 |
| CTCCGTACGA | GGGTGACGAG | TCCTTCCTGG | CTGGCGCTAC | TGAAGCGACC | ACCACCCTGT | 1560 |
| GGGACAAAGT | AATGGAAGGC | GTTAAACTGG | AAAACCGCAC | TCACGCGCCA | GTTGACTTTG | 1620 |
| ACACCGCTGT | TGCTTCCACC | ATCACCTCTC | ACGACGCTGG | CTACATCAAC | AAGCAGCTTG | 1680 |
| AGAAAATCGT | TGGTCTGCAG | ACTGAAGCTC | CGCTGAAACG | TGCTCTTATC | CCGTTCGGTG | 1740 |
| GTATCAAAAT | GATCGAAGGT | TCCTGCAAAG | CGTACAACCG | CGAACTGGAT | CC | 1792 |